United States Patent
Lustbader

(10) Patent No.: US 7,202,215 B2
(45) Date of Patent: Apr. 10, 2007

(54) LONG-ACTING FOLLICLE STIMULATING HORMONE ANALOGUES AND USES THEREOF

(75) Inventor: Joyce Lustbader, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 294 days.

(21) Appl. No.: 10/357,252

(22) Filed: Jan. 31, 2003

(65) Prior Publication Data

US 2003/0211580 A1 Nov. 13, 2003

Related U.S. Application Data

(63) Continuation-in-part of application No. 10/112,321, filed on Mar. 27, 2002, which is a continuation-in-part of application No. 10/062,910, filed on Jan. 31, 2002, now abandoned.

(51) Int. Cl.
*A61K 38/16* (2006.01)
*A61K 38/00* (2006.01)
*A61K 38/02* (2006.01)
*C07K 2/00* (2006.01)
*C07K 7/08* (2006.01)

(52) U.S. Cl. .......................... 514/13; 514/2; 530/300; 530/326

(58) Field of Classification Search .................. None
See application file for complete search history.

(56) References Cited

U.S. PATENT DOCUMENTS

| 5,585,345 A | 12/1996 | Boime | 514/8 |
|---|---|---|---|
| 5,712,122 A | 1/1998 | Boime et al. | |
| 5,759,818 A | 6/1998 | Boime | 435/69.7 |
| 5,958,737 A | 9/1999 | Boime et al. | |
| 5,985,611 A | 11/1999 | Boime | 435/69.4 |
| 6,225,449 B1 | 5/2001 | Boime | 530/398 |
| 6,242,580 B1 | 6/2001 | Boime et al. | 530/398 |
| 6,306,654 B1 | 10/2001 | Boime et al. | 435/360 |

OTHER PUBLICATIONS

P. Wynn, et al. Human Reprod. (1998) 13(11), pp. 3132-3138.*
E.H.Y. Ng, et al. Human Reprod. (2001) 16(2), pp. 319-325.*
H.J. Out, et al. Human Reprod. (2000) 15(1), pp. 29-35.*
R.R. Yeoman, et al. Biol. Reprod. (1994) 50, pp. 329-335.*
K.B. Gilchrist, et al. Biol. Reprod. (1997) 56, pp. 238-246.*
B. Frydman, et al. Human Reprod. (2000) 15(3), pp. 520-525.*
A.L. Mikkelsen, et al. Human Reprod. (2000) 15(8), pp. 1685-1690.*
Bouloux, P. M., D. J. Handelsman, F. Jockenhovel, E. Nieschlag, J. Rabinovici, W. L. Frasa, J. J. de Bie, G. Voortman, and J. Itskovitz-Eldor (2001) First human exposure to FSH-CTP in hypogonadotrophic hypogonadal males. *Hum. Reprod.* 16, 1592-1597.

Calvo, F. O., H. T. Keutmann, E. R. Bergert, and R. J. Ryan (1986) Deglycosylated human follitropin: characterization and effects on adenosine cyclic 3',5'-phosphate production in porcine granulosa cells. *Biochemistry* 25, 3938-3943.

Chui, D. K., N. D. Pugh, S. M. Walker, L. Gregory, and R. W. Shaw (1997) Follicular vascularity-the predictive value of transvaginal power Doppler ultrasonography in an in vitro fertilization programme: a preliminary study. *Hum. Reprod.* 12, 191-196.

Dissen, G. A., H. E. Lara, W. H. Fahrenbach, M. E. Costa, and S. R. Ojeda (1994) Immature rat ovaries become revascularized rapidly after autotransplantation and show a gonadotropin-dependent increase in angiogenic factor gene expression. *Endocrinology* 134, 1146-1154.

Fares, F. A., N. Suganuma, K. Nishimori, P. S. Lapolt, A. J. Hsueh, and I. Boime (1992) Design of a long-acting follitropin agonist by fusing the C-terminal sequence of the chorionic gonadotropin beta subunit to the follitropin beta subunit. *Proc. Natl. Acad. Sci. U.S.A.* 89, 4304-4308.

Feng, W., M. M. Matzuk, K. Mountjoy, E. Bedows, R. W. Ruddon, and I. Boime (1995) The asparagine-linked oligosaccharides of the human chorionic gonadotropin beta subunit facilitate correct disulfide bond pairing. *J. Biol. Chem.* 270, 11851-11859.

Ferrara, N., H. Chen, T. Davis-Smyth, H. P. Gerber, T. N. Nguyen, D. Peers, V. Chisholm, K. J. Hillan, and R. H. Schwall (1998) Vascular endothelial growth factor is essential for corpus luteum angiogenesis. *Nat. Med.* 4, 336-340.

Ferrara, N., K. Houck, L. Jakeman, and D. W. Leung (1992) Molecular and biological properties of the vascular endothelial growth factor family of proteins. *Endocr. Rev.* 13, 18-32.

Krichevsky, A., S. Birken, J. F. O'Connor, K. Bikel, J. Schlatterer, and R. E. Canfield (1994) The development of a panel of monoclonal antibodies to human luteinizing hormone and its application to immunological mapping and two-site assays. *Endocrine* 2, 511-520.

LeContonnec, J.Y., H.C. Porchet, V. Beltrami, A. Khan, S. Toon, and M. Rowland (1994) Clinical pharmacology of recombinant human follicle-stimulating hormone. II. Single doses and steady-state pharmacokinetics. *Fertil. Steril.* 61, 679-86.

Lindau-Shapard, B.A., H.A. Brumberg, A.J. Peterson, and J.A. Dias (2001) Reversible immunoneutralization of human follitropin receptor. *J. Reprod. Immun.* 49, 1-19.

Matzuk, M. M., A. J. Hsueh, P. Lapolt, A. Tsafriri, J. L. Keene, and I. Boime (1990) The biological role of the carboxyl-terminal extension of human chorionic gonadotropin beta-subunit. *Endocrinology* 126, 376-383.

Nargund, G., T. Bourne, P. Doyle, J. Parsons, W. Cheng, S. Campbell, and W. Collins (1996) Associations between ultrasound indices of follicular blood flow, oocyte recovery and preimplantation embryo quality. *Hum. Reprod.* 11, 109-113.

(Continued)

*Primary Examiner*—Cecilia J. Tsang
*Assistant Examiner*—Andrew D. Kosar
(74) *Attorney, Agent, or Firm*—John P. White; Cooper & Dunham LLP

(57) ABSTRACT

This invention provides FSH analogues having increased serum half-life relative to FSH. This invention also provides related compositions and methods for increasing fertility, egg production and spermatogenesis in a subject.

18 Claims, 21 Drawing Sheets

OTHER PUBLICATIONS

Pedersen, T. and H. Peters (1968) Proposal for a classification of oocytes and follicles in the mouse ovary. *J. Reprod. Fertil.* 17, 555-557.

Pierce, J. G. and T. F. Parsons (1981) Glycoprotein hormones: structure and function. *Annu. Rev. Biochem.* 50, 465-495.

Porchet, H.C., J.Y. LeContonnec, B. Neuteboom, S. Canali, and G. Zanolo (1995) Pharmacokinetics of recombinant human luteinizing hormone. *J. Clin. Endocrinol. Metab.* 80, 667-73.

Saal, W., H.J. Glowania, and J. Happ (1991) Pharmacodynamics and pharmacokinetics after subcutaneous and intramuscular injection of human chorionic gonadotropin. *Fertil. Steril.* 56, 225-8.

Sairam, M. R. and P. Manjunath (1982) Studies on pituitary follitropin. XL Induction of hormonal antagonistic activity by chemical deglycosylation. *Mol. Cell Endocrinol.* 28, 139-150.

Sugahara, T., M. R. Pixley, F. Fares, and I. Boime (1996) Characterization of the O-glycosylation sites in the chorionic gonadotropin beta subunit in vivo using site-directed mutagenesis and gene transfer. *J. Biol. Chem.* 271, 20797-20804.

Suganuma, N., M. M. Matzuk, and I. Boime (1989) Elimination of disulfide bonds affects assembly and secretion of the human chorionic gonadotropin beta subunit. *J. Biol. Chem.* 264, 19302-19307.

Van Blerkom, J., M. Antczak, and R. Schrader (1997) The developmental potential of the human oocyte is related to the dissolved oxygen content of follicular fluid: association with vascular endothelial growth factor levels and perifollicular blood flow characteristics. *Hum. Reprod.* 12, 1047-1055; and.

Yen, S. S., O. Llerena, B. Little, and O. H. Pearson (1968) Disappearance rates of endogenous luteinizing hormone and chorionic gonadotropin in man. *J. Clin. Endocrinol. Metab.* 28, 1763-1767.

International Search Report issued Dec. 1, 2003 in connection with PCT International Application No. PCT/US03/02982: and.

Ben-Menahem et al. (2001) The Position of the Alpha and Beta Subunits in a Single Chain Variant of Human Chorionic Gonadotropin Affects the Heterodimeric Interaction of the Subunits and Receptor-Binding Epitope. J. Biol. Chem. 276:29871-879.

* cited by examiner

Figure 1

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1            5                   10                  15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa
192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg
288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt
336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
    130                 135                 140 gga tcc taa
            441
Gly Ser
145
```

Figure 2

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa
192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg
288
Val Pro Gly Cys Ala His His Ala Asp Ser Leu Tyr Thr Tyr Pro Val
            85                  90                  95 gcc acc cag tgt cac tgt ggc aag tgt gac agc gac agc act gat tgt
336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
            115                 120                 125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
    130                 135                 140 aga tcc gga tcg aac gcg acg ggg tca ggt tct aat gca act tca gga
480
Arg Ser Gly Ser Asn Ala Thr Gly Ser Gly Ser Asn Ala Thr Ser Gly
145                 150                 155                 160 tcc taa
        486
Ser
```

Figure 3

| | | | | | | | | | | | | | | | | |
|---|---|---|---|---|---|---|---|---|---|---|---|---|---|---|---|---|
| atg | aag | aca | ctc | cag | ttt | ttc | ttc | ctt | ttc | tgt | tgc | tgg | aaa | gca | atc | 48 |
| Met | Lys | Thr | Leu | Gln | Phe | Phe | Phe | Leu | Phe | Cys | Cys | Trp | Lys | Ala | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tgc | tgc | aat | agc | tgt | gag | ctg | acc | aac | atc | acc | att | gca | ata | gag | aaa | 96 |
| Cys | Cys | Asn | Ser | Cys | Glu | Leu | Thr | Asn | Ile | Thr | Ile | Ala | Ile | Glu | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| gaa | gaa | tgt | cgt | ttc | tgc | ata | agc | atc | aac | acc | act | tgg | tgt | gct | ggc | 144 |
| Glu | Glu | Cys | Arg | Phe | Cys | Ile | Ser | Ile | Asn | Thr | Thr | Trp | Cys | Ala | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| tac | tgc | tac | acc | agg | gat | ctg | gtg | tat | aag | gac | cca | gcc | agg | ccc | aaa | 192 |
| Tyr | Cys | Tyr | Thr | Arg | Asp | Leu | Val | Tyr | Lys | Asp | Pro | Ala | Arg | Pro | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| atc | cag | aaa | aca | tgt | acc | ttc | aag | gaa | ctg | gta | tat | gaa | aca | gtg | aga | 240 |
| Ile | Gln | Lys | Thr | Cys | Thr | Phe | Lys | Glu | Leu | Val | Tyr | Glu | Thr | Val | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtg | ccc | ggc | tgt | gct | cac | cat | gca | gat | tcc | ttg | tat | aca | tac | cca | gtg | 288 |
| Val | Pro | Gly | Cys | Ala | His | His | Ala | Asp | Ser | Leu | Tyr | Thr | Tyr | Pro | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| gcc | acc | cag | tgt | cac | tgt | ggc | aag | tgt | gac | agc | gac | agc | act | gat | tgt | 336 |
| Ala | Thr | Gln | Cys | His | Cys | Gly | Lys | Cys | Asp | Ser | Asp | Ser | Thr | Asp | Cys | |
| | | | 100 | | | | | 105 | | | | | 110 | | | |

| | | | | | | | | | | | | | | | | |
|---|---|---|---|---|---|---|---|---|---|---|---|---|---|---|---|---|
| act | gtg | cga | ggc | ctg | ggg | ccc | agc | tac | tgc | tcc | ttt | ggt | gaa | atg | aaa | 384 |
| Thr | Val | Arg | Gly | Leu | Gly | Pro | Ser | Tyr | Cys | Ser | Phe | Gly | Glu | Met | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| gaa | gga | tcc | ccc | cgc | ttc | cag | gac | tcc | tct | tcc | tca | aag | gcc | cct | ccc | 432 |
| Glu | Gly | Ser | Pro | Arg | Phe | Gln | Asp | Ser | Ser | Ser | Ser | Lys | Ala | Pro | Pro | |
| | 130 | | | | | 135 | | | | | 140 | | | | | |

| | | | | | | | | | | | | | | | | |
|---|---|---|---|---|---|---|---|---|---|---|---|---|---|---|---|---|
| ccc | agc | ctt | cca | agc | cca | tcc | cga | ctc | ccg | ggg | ccc | tcg | gac | acc | ccg | 480 |
| Pro | Ser | Leu | Pro | Ser | Pro | Ser | Arg | Leu | Pro | Gly | Pro | Ser | Asp | Thr | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| atc | ctc | cca | caa | act | agt | gct | cct | gat | gtg | cag | gat | tgc | cca | gaa | tgc | 528 |
| Ile | Leu | Pro | Gln | Thr | Ser | Ala | Pro | Asp | Val | Gln | Asp | Cys | Pro | Glu | Cys | |
| | | | | 165 | | | | | 170 | | | | | 175 | | |

| | | | | | | | | | | | | | | | | |
|---|---|---|---|---|---|---|---|---|---|---|---|---|---|---|---|---|
| acg | cta | cag | gaa | aac | cca | ttc | ttc | tcc | cag | ccg | ggt | gcc | cca | ata | ctt | 576 |
| Thr | Leu | Gln | Glu | Asn | Pro | Phe | Phe | Ser | Gln | Pro | Gly | Ala | Pro | Ile | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| cag | tgc | atg | ggc | tgc | tgc | ttc | tct | aga | gca | tat | ccc | act | cca | cta | agg | 624 |
| Gln | Cys | Met | Gly | Cys | Cys | Phe | Ser | Arg | Ala | Tyr | Pro | Thr | Pro | Leu | Arg | |
| | | 195 | | | | | 200 | | | | | 205 | | | | |

| | | | | | | | | | | | | | | | | |
|---|---|---|---|---|---|---|---|---|---|---|---|---|---|---|---|---|
| tcc | aag | aag | acg | atg | ttg | gtc | caa | aag | aac | gtc | acc | tca | gag | tcc | act | 672 |
| Ser | Lys | Lys | Thr | Met | Leu | Val | Gln | Lys | Asn | Val | Thr | Ser | Glu | Ser | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| tgc | tgt | gta | gct | aaa | tca | tat | aac | agg | gtc | aca | gta | atg | ggg | ggt | ttc | 720 |
| Cys | Cys | Val | Ala | Lys | Ser | Tyr | Asn | Arg | Val | Thr | Val | Met | Gly | Gly | Phe | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aaa | gtg | gag | aac | cac | acg | gcg | tgc | cac | tgc | agt | act | tgt | tat | tat | cac | 768 |
| Lys | Val | Glu | Asn | His | Thr | Ala | Cys | His | Cys | Ser | Thr | Cys | Tyr | Tyr | His | |
| | | | | 245 | | | | | 250 | | | | | 255 | | |

| | | | |
|---|---|---|---|
| aaa | tct | taa | 777 |
| Lys | Ser | | |

Figure 4

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa
192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg
288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt
336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
    130                 135                 140 gga tcc act agt gct cct gat gtg cag gat tgc cca gaa tgc acg cta
480
Gly Ser Thr Ser Ala Pro Asp Val Gln Asp Cys Pro Glu Cys Thr Leu
145                 150                 155                 160 cag gaa aac cca ttc ttc tcc cag ccg ggt gcc cca ata ctt cag tgc
528
Gln Glu Asn Pro Phe Phe Ser Gln Pro Gly Ala Pro Ile Leu Gln Cys
                165                 170                 175 atg ggc tgc tgc ttc tct aga gca tat ccc act cca cta agg tcc aag
576
Met Gly Cys Cys Phe Ser Arg Ala Tyr Pro Thr Pro Leu Arg Ser Lys
            180                 185                 190 aag acg atg ttg gtc caa aag aac gtc acc tca gag tcc act tgc tgt
624
Lys Thr Met Leu Val Gln Lys Asn Val Thr Ser Glu Ser Thr Cys Cys
        195                 200                 205 gta gct aaa tca tat aac agg gtc aca gta atg ggg ggt ttc aaa gtg
672
Val Ala Lys Ser Tyr Asn Arg Val Thr Val Met Gly Gly Phe Lys Val
    210                 215                 220 gag aac cac acg gcg tgc cac tgc agt act tgt tat tat cac aaa tct
720
Glu Asn His Thr Ala Cys His Cys Ser Thr Cys Tyr Tyr His Lys Ser
225                 230                 235                 240 taa
723
```

Figure 5

| | |
|---|---|
| atg aag aca ctc cag ttt ttc ttc ctt ttc tgt tgc tgg aaa gca atc<br>Met Lys Thr Leu Gln Phe Phe Phe Leu Phe Cys Cys Trp Lys Ala Ile<br>1                5                          10                      15 | 48 |
| tgc tgc aat agc tgt gag ctg acc aac atc acc att gca ata gag aaa<br>Cys Cys Asn Ser Cys Glu Leu Thr Asn Ile Thr Ile Ala Ile Glu Lys<br>            20                        25                      30 | 96 |
| gaa gaa tgt cgt ttc tgc ata agc atc aac acc act tgg tgt gct ggc<br>Glu Glu Cys Arg Phe Cys Ile Ser Ile Asn Thr Thr Trp Cys Ala Gly<br>              35                   40                  45 | 144 |
| tac tgc tac acc agg gat ctg gtg tat aag gac cca gcc agg ccc aaa<br>Tyr Cys Tyr Thr Arg Asp Leu Val Tyr Lys Asp Pro Ala Arg Pro Lys<br>    50                    55                      60 | 192 |
| atc cag aaa aca tgt acc ttc aag gaa ctg gta tat gaa aca gtg aga<br>Ile Gln Lys Thr Cys Thr Phe Lys Glu Leu Val Tyr Glu Thr Val Arg<br>65                    70                      75                80 | 240 |
| gtg ccc ggc tgt gct cac cat gca gat tcc ttg tat aca tac cca gtg<br>Val Pro Gly Cys Ala His His Ala Asp Ser Leu Tyr Thr Tyr Pro Val<br>                85                      90                      95 | 288 |
| gcc acc cag tgt cac tgt ggc aag tgt gac agc gac agc act gat tgt<br>Ala Thr Gln Cys His Cys Gly Lys Cys Asp Ser Asp Ser Thr Asp Cys<br>            100                      105                  110 | 336 |
| act gtg cga ggc ctg ggg ccc agc tac tgc tcc ttt ggt gaa atg aaa<br>Thr Val Arg Gly Leu Gly Pro Ser Tyr Cys Ser Phe Gly Glu Met Lys<br>            115                      120                  125 | 384 |
| gaa gga tcc gga tcg aac gcg acg ggg tca ggt tct aat gca act tca<br>Glu Gly Ser Gly Ser Asn Ala Thr Gly Ser Gly Ser Asn Ala Thr Ser<br>     130                    135                    140 | 432 |
| aga tcc gga tcg aac gcg acg ggg tca ggt tct aat gca act tca gga<br>Arg Ser Gly Ser Asn Ala Thr Gly Ser Gly Ser Asn Ala Thr Ser Gly<br>145                  150                    155                  160 | 480 |
| tcc act agt gct cct gat gtg cag gat tgc cca gaa tgc acg cta cag<br>Ser Thr Ser Ala Pro Asp Val Gln Asp Cys Pro Glu Cys Thr Leu Gln<br>                165                      170                  175 | 528 |
| gaa aac cca ttc ttc tcc cag ccg ggt gcc cca ata ctt cag tgc atg<br>Glu Asn Pro Phe Phe Ser Gln Pro Gly Ala Pro Ile Leu Gln Cys Met<br>            180                      185                  190 | 576 |
| ggc tgc tgc ttc tct aga gca tat ccc act cca cta agg tcc aag aag<br>Gly Cys Cys Phe Ser Arg Ala Tyr Pro Thr Pro Leu Arg Ser Lys Lys<br>            195                      200                  205 | 624 |
| acg atg ttg gtc caa aag aac gtc acc tca gag tcc act tgc tgt gta<br>Thr Met Leu Val Gln Lys Asn Val Thr Ser Glu Ser Thr Cys Cys Val<br>            210                      215                  220 | 672 |
| gct aaa tca tat aac agg gtc aca gta atg ggg ggt ttc aaa gtg gag<br>Ala Lys Ser Tyr Asn Arg Val Thr Val Met Gly Gly Phe Lys Val Glu<br>225                  230                    235                  240 | 720 |
| aac cac acg gcg tgc cac tgc agt act tgt tat tat cac aaa tct taa<br>Asn His Thr Ala Cys His Cys Ser Thr Cys Tyr Tyr His Lys Ser<br>                245                      250                  255 | 768 |

Figure 12

Beta hCG

```
  1                            10          CHO
Ser-Lys-Glu-Pro-Leu-Arg-Pro-Arg-Cys-Arg-Pro-Ile-Asn-Ala-Thr-Leu-Ala-
           20                           CHO
Val-Glu-Lys-Glu-Gly-Cys-Pro-Val-Cys-Ile-Thr-Val-Asn-Thr-Thr-Ile-Cys-
                    40                                50
Ala-Gly-Tyr-Cys-Pro-Thr-Met-Thr-Arg-Val-Leu-Gln-Gly-Val-Leu-Pro-Ala-
                         60
Leu-Pro-Gln-Val-Val-Cys-Asn-Tyr-Arg-Asp-Val-Arg-Phe-Glu-Ser-Ile-Arg-
      70                              80
Leu-Pro-Gly-Cys-Pro-Arg-Gly-Val-Asn-Pro-Val-Val-Ser-Tyr-Ala-Val-Ala-
                90                                   100
Leu-Ser-Cys-Gln-Cys-Ala-Leu-Cys-Arg-Arg-Ser-Thr-Thr-Asp-Cys-Gly-Gly-
                              110
Pro-Lys-Asp-His-Pro-Leu-Thr-Cys-Asp-Asp-Pro-Arg-Phe-Gln-Asp-Ser-Ser-
 120    CHO                CHO           130     CHO
Ser-Ser-Lys-Ala-Pro-Pro-Pro-Ser-Leu-Pro-Ser-Pro-Ser-Arg-Leu-Pro-Gly-
     CHO    140              145
Pro-Ser-Asp-Thr-Pro-Ile-Leu-Pro-Gln
```

Figure 13
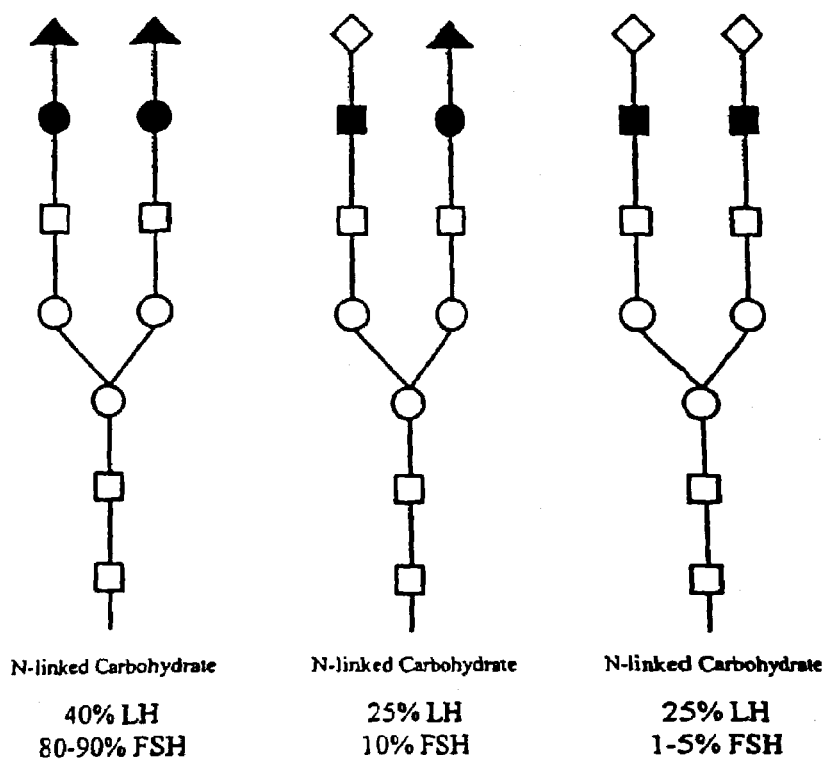
N-linked Carbohydrate
40% LH
80-90% FSH
N-linked Carbohydrate
25% LH
10% FSH
N-linked Carbohydrate
25% LH
1-5% FSH
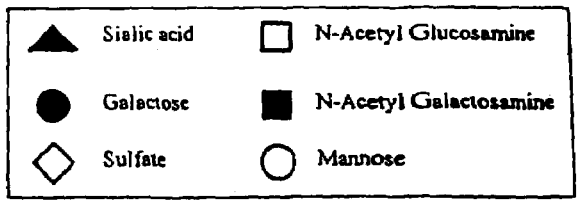

Figure 14
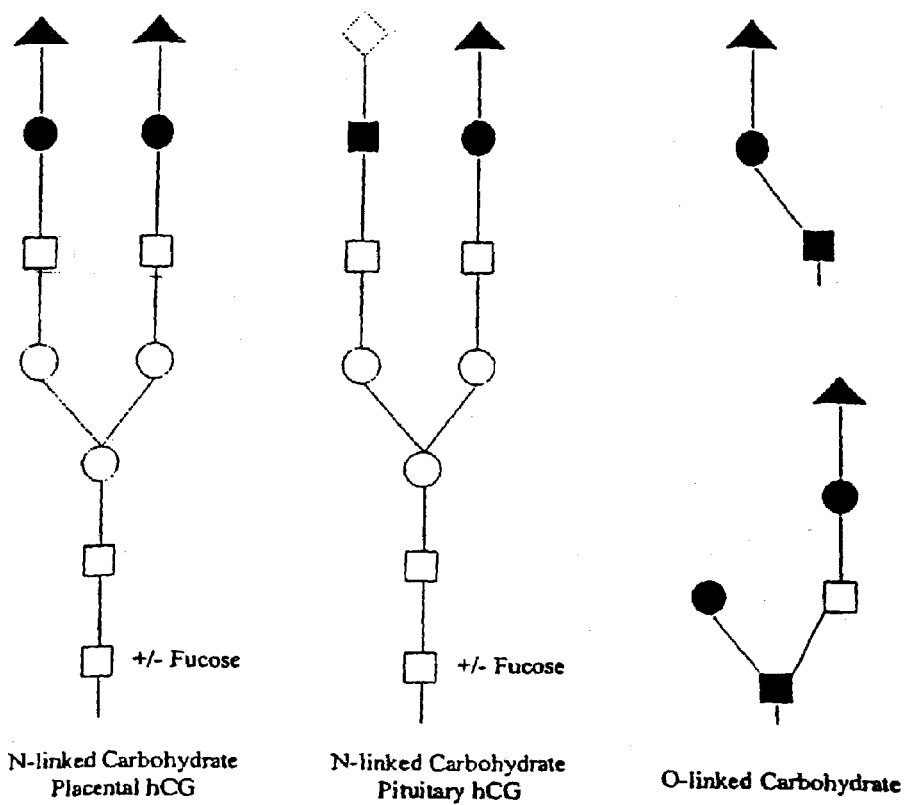
N-linked Carbohydrate
Placental hCG
N-linked Carbohydrate
Pituitary hCG
O-linked Carbohydrate
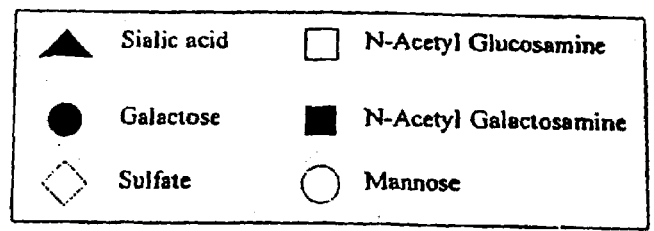

Figure 15

```
        M   K   T   L   Q   F   F   F   L   F   C   C   W
  1   atg aag aca ctc cag ttt ttc ttc ctt ttc tgt tgc tgg   39

K   A   I   C   C   N   S   C   E   L   T   N   I
  40  aaa gca atc tgc tgc aat agc tgt gag ctg acc aac atc   78

T   I   A   I   E   K   E   E   C   R   F   C   I
  79  acc att gca ata gag aaa gaa gaa tgt cgt ttc tgc ata  117

S   I   N   T   T   W   C   A   G   Y   C   Y   T
 118  agc atc aac acc act tgg tgt gct ggc tac tgc tac acc  156

R   D   L   V   Y   K   D   P   A   R   P   K   I
 157  agg gat ctg gtg tat aag gac cca gcc agg ccc aaa atc  195

Q   K   T   C   T   F   K   E   L   V   Y   E   T
 196  cag aaa aca tgt acc ttc aag gaa ctg gta tat gaa aca  234

V   R   V   P   G   C   A   H   H   A   D   S   L
 235  gtg aga gtg ccc ggc tgt gct cac cat gca gat tcc ttg  273

Y   T   Y   P   V   A   T   Q   C   H   C   G   K
 274  tat aca tac cca gtg gcc acc cag tgt cac tgt ggc aag  312

C   D   S   D   S   T   D   C   T   V   R   G   L
 313  tgt gac agc gac agc act gat tgt act gtg cga ggc ctg  351

G   P   S   Y   C   S   F   G   E   M   K   E   *
 352  ggg ccc agc tac tgc tcc ttt ggt gaa atg aaa gaa taa  390

```
      M   D   Y   Y   R   K   Y   A   A   I   F   L   V
  1   atg gat tac tac aga aaa tat gca gct atc ttt ctg gtc    39

T   L   S   V   F   L   H   V   L   H   S   A   P
 40   aca ttg tcg gtg ttt ctg cat gtt ctc cat tcc gct cct    78

D   V   Q   D   C   P   E   C   T   L   Q   E   N
 79   gat gtg cag gat tgc cca gaa tgc acg cta cag gaa aac    117

P   F   F   S   Q   P   G   A   P   I   L   Q   C
118   cca ttc ttc tcc cag ccg ggt gcc cca ata ctt cag tgc    156

M   G   C   C   F   S   R   A   Y   P   T   P   L
157   atg ggc tgc tgc ttc tct aga gca tat ccc act cca cta    195

R   S   K   K   T   M   L   V   Q   K   N   V   T
196   agg tcc aag aag acg atg ttg gtc caa aag aac gtc acc    234

S   E   S   T   C   C   V   A   K   S   Y   N   R
235   tca gag tcc act tgc tgt gta gct aaa tca tat aac agg    273

V   T   V   M   G   G   F   K   V   E   N   H   T
274   gtc aca gta atg ggg ggt ttc aaa gtg gag aac cac acg    312

A   C   H   C   S   T   C   Y   Y   H   K   S   *
313   gcg tgc cac tgc agt act tgt tat tat cac aaa tct taa    351
```

LONG-ACTING FOLLICLE STIMULATING HORMONE ANALOGUES AND USES THEREOF

This application is a continuation-in-part of U.S. Ser. No. 10/112,321, filed Mar. 27, 2002, now U.S. Pat. No. 7,081,446 B2, issued Jul. 25, 2006, which is a continuation-in-part of U.S. Ser. No. 10/062,910, filed Jan. 31, 2002, now abandoned, the contents of which are hereby incorporated by reference.

The invention described herein was made with government support under grant number DK-51266 from the National Institutes of Health. Accordingly, the United States government has certain rights in this invention.

Throughout this application, various publications are referenced by author and publication date. Full citations for these publications may be found at the end of the specification immediately preceding the claims. The disclosure of these publications is hereby incorporated by reference into this application to describe more fully the art to which this invention pertains.

BACKGROUND OF THE INVENTION

The pituitary glycoprotein hormone, follicle stimulating hormone (FSH), is a heterodimer comprised of two non-covalently bound subunits, α and β (Pierce et al., 1981). The α-subunit is interchangeable among the hormones of this family, which include luteinizing hormone (LH), thyrotropin stimulating hormone (TSH) and chorionic gonadotropin (CG), in addition to FSH. The β-subunit, on the other hand, is unique to each hormone and is primarily responsible for the biological specificity of hormone action (see FIG. 15 respectively).

Human FSH (hFSH) contains four N-linked carbohydrate moieties, two on each of the α- and β-subunits. A schematic of the carbohydrate moieties on hLH and hFSH is shown in FIG. 13. While the functional significance of these moieties is poorly understood, they are likely to be important for proper protein folding, subunit assembly and secretion of the hormone (Suganuma et al. 1989; Feng et al., 1995). The carbohydrate moieties may also be obligatory for signal transduction, although partially deglycosylated hormones show preserved receptor binding (Calve et al., 1986; Sairam et al., 1982).

Current pharmacologic formulations of hFSH include purified urinary derivatives and, more recently, recombinant human FSH (rhFSH). rhFSH is used clinically in the treatment of infertility and in gonadotropin replacement therapy. However, the recombinant protein suffers from a short serum half-life and correspondingly diminished biopotency, necessitating frequent administration and limiting its clinical usefulness. For example, rhFSH must be administered as a daily intramuscular or subcutaneous injection, often for 8 to 12 days when used for ovulation induction (LeContonnec et al., 1994). These regimens are associated with a number of side effects, including local irritation and discomfort, which result in poor compliance and a reduction in therapeutic efficacy. One possibility for overcoming this limitation is to increase or alter the glycosylation profile of the recombinant protein in a manner that would improve its pharmacokinetic profile and in vivo bioactivity (see Baird et al., 2001).

The first reported attempt to produce an improved rhFSH by increasing the glycosylation of the protein was the synthesis of a hybrid β-FSH subunit containing the carboxy-terminal peptide (CTP) sequence of hCG (Fares et al., 1992). Among the glycoprotein hormones, hCG is known to have the longest circulating half-life. This has been attributed to the presence of four O-linked glycosylation sites on the CTP of its β-subunit, corresponding to amino acids 113–145 (Matzuk et al., 1990). Thus, the rationale for constructing a hybrid β-FSH subunit linked to the CTP was that the CTP would confer an increased serum half-life on the recombinant FSH protein. This prediction was supported by the finding that the protein (β-FSH-CTP) was able to dimerize with a coexpressed α-FSH subunit to produce a functional hormone with an increased half-life. Importantly, this β-FSH-CTP demonstrated similar in vitro bioactivity and substantially increased in vivo bioactivity compared with preparations of native hFSH.

Two recently published studies lend further support for the potential clinical usefulness of long-acting FSH proteins. The first study reported the results of hormone replacement therapy in a trial with hypogonadotropic hypogonadal men (Bouloux et al., 2001). The second reported the results of hormone replacement therapy in healthy, pituitary-suppressed female subjects (Duijker et al., 2002). Both trials demonstrated that the elimination half-life of β-FSH-CTP was increased relative to rhFSH and supported the prediction that long-acting FSH proteins could reduce the frequency of hormone injections required to achieve the desired clinical outcome.

In contrast with N-linked sugars, deglycosylation of O-linked moieties does not affect signal transduction, and hCG devoid of this extension maintains its in vitro bioactivity. Schematic examples of N-linked and O-linked carbohydrates are shown in FIG. 14.

Instead, the importance of the O-linked sugars lies in providing enhanced stability of the hormone in vivo. This was initially deduced from comparisons between hCG and hLH, whose biological activity and β subunits are remarkably similar but whose serum half lives are dramatically different. The β subunits of hCG and hLH share greater than 85% sequence identity through the N-terminal 113 amino acids (Pierce et al., 1981). In addition, these two hormones share a common receptor and elicit similar biologic activity following receptor binding. However, the serum half-life of hCG is almost five-times that of hLH (Porchet et al., 1995; Saal et al., 1991; Yen et al., 1968). The primary structural difference between β-hCG and β-hLH is the additional carboxy-terminal amino acids comprising the CTP sequence of β-hCG. This carboxy-terminal peptide, specifically its O-linked glycosylation sequences, is thus likely to be responsible for both the decreased metabolism and excretion of hCG, and thus also for its notably increased serum half-life over the relatively transient hLH.

The importance of the CTP in promoting hormone stability was demonstrated by the synthetic β-FSH-CTP protein discussed above. Thus, merely adding the CTP sequence to β-hFSH was sufficient to increase the biological activity of the hormone, most likely through an increase in serum-half life. Indeed, recent pharmacokinetic parameter estimates in humans have demonstrated that the β-hFSH-CTP protein has an elimination half-life of 2 to 3 times longer than that of native recombinant hFSH (Bouloux et al., 2001). Unfortunately, an early attempt to further increase the half-life and bioactivity of the β-hFSH-CTP protein by adding two tandem repeats of CTPs was unsuccessful (LaPolt et al., 1992). Thus, efforts to further improve the pharmacokinetics and bioactivity of β-FSH-CTP by adding additional CTP moieties were abandoned.

SUMMARY OF THE INVENTION

This invention provides a synthetic FSH comprising a β-FSH subunit, an α-FSH subunit and a half-life-increasing moiety, wherein the β-FSH subunit, α-FSH subunit and half-life-increasing moiety are covalently bound.

This invention also provides a synthetic FSR comprising a β-FSH subunit covalently bound to a polypeptide segment comprising the amino acid sequence ser-gly-ser-asn-ala-thr-gly-ser-gly-ser-asn-ala-thr-ser-gly-ser (SEQ. ID. NO:16).

This invention also provides a synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ. ID. NO:16), wherein the β-FSH subunit, α-FSH subunit and polypeptide segment are covalently bound.

This invention also provides a pharmaceutical composition comprising a synthetic FSH of the instant invention and a pharmaceutically acceptable carrier.

This invention further provides an article of manufacture comprising (a) the instant pharmaceutical composition, and (b) a label and/or instructions indicating a use of the pharmaceutical composition for the enhancement of fertility, egg production and/or spermatogenesis.

This invention provides nucleic acids encoding the instant synthetic FSH polypeptides, as well as expression vectors and suitable host cells for expressing these polypeptides.

This invention also provides a method for producing the polypeptides of the instant invention that comprises growing a suitable host cell transfected with a vector encoding the polypeptide under conditions permitting its expression and recovering the polypeptide so expressed.

This invention additionally provides a method for producing a synthetic FSH, which comprises co-expressing (i) a nucleic acid which encodes an α-FSH subunit, and (ii) a nucleic acid which encodes a polypeptide comprising a β-FSH subunit and a polypeptide segment comprising the amino acid sequence ser-gly-ser-asn-ala-thr-gly-ser-gly-ser-asn-ala-thr-ser-gly-ser (SEQ. ID. NO:16), under conditions permitting such co-expression; and recovering the synthetic FSH so produced.

This invention provides a method for increasing a subject's fertility which comprises administering to the subject an amount of the instant synthetic FSH effective to enhance the subject's fertility.

This invention also provides a method for increasing a subject's spermatogenesis which comprises administering to the subject an amount of the instant synthetic FSH effective to enhance the subject's spermatogenesis.

This invention also provides a method for increasing a subject's egg production which comprises administering to the subject an amount of the instant synthetic FSH effective to enhance the subject's egg production.

This invention also provides a method of increasing the half-life of a molecule in a subject, which method comprises glycosylating the molecule in a manner effective to increase the molecule's half-life.

This invention further provides a method for increasing the level of inhibin-A in a subject which comprises administering to the subject an amount the instant synthetic FSH effective to increase the subject's inhibin-A level.

This invention also provides a method for increasing the quality of an oocyte which comprises contacting the oocyte with an amount of the instant synthetic FSH effective to increase the quality of the oocyte.

Finally, this invention provides a method for increasing the quality of an oocyte in a subject which comprises administering to the subject an amount of the instant synthetic FSH effective to increase the quality of the oocyte in the subject.

BRIEF DESCRIPTION OF THE FIGURES

FIG. 1: Nucleotide (SEQ. ID. NO:1) and predicted amino acid sequence (SEQ. ID. NO:2) of the fusion protein β-hFSH-N2. The N2 sequence is amino acids 130 through 146.

FIG. 2: Nucleotide (SEQ. ID. NO:3) and predicted amino acid sequence (SEQ. ID. NO:4) of the fusion protein β-hFSH-N4. The N4 sequence is amino acids 130 through 161.

FIG. 3: Nucleotide (SEQ. ID. NO:5) and predicted amino acid sequence (SEQ. ID. NO:6) of the fusion protein β-hFSH-CTP-α-hFSH.

FIG. 4: Nucleotide (SEQ. ID. NO:7) and predicted amino acid sequence (SEQ. ID. NO:8) of the fusion protein β-hFSH-N2-α-hFSH.

FIG. 5: Nucleotide (SEQ. ID. NO:9) and predicted amino acid sequence (SEQ. ID. NO:10) of the fusion protein β-hFSH-N4-α-hFSH.

FIG. 12: Amino acid sequence of β-hCG (SEQ. ID. NO:11), wherein CHO is a glycosylation site and the black shading corresponds to the CTP. N-linked glycosylation is present on Asn, and O-linked glycosylation is present on Ser.

FIG. 13: Schematic of the carbohydrate moieties on both hLH and hFSH and some of the microheterogeneity which results in the wide range of isoelectric points in the glycoprotein hormones.

FIG. 14: Schematic examples of N-linked and O-linked carbohydrates.

FIG. 15: Nucleotide (SEQ. ID. NO:12) and amino acid sequence (SEQ. ID. NO:13) of β-hFSH. The signal sequence corresponds to the sequence beginning with the methionine at position 1 and ending with the cysteine at position 18.

FIG. 16: Nucleotide (SEQ. ID. NO:14) and amino acid sequence (SEQ. ID. NO:15) of α-hFSH. The signal sequence corresponds to the sequence beginning with the methionine at position 1 and ending with the serine at position 24.

FIG. 18: Mean serum hFSH concentration-time profiles following a single IV injection of the indicated hFSH. Twenty-one day old female rats were injected at a dose of 2800 ng/rat. (n=3)

DETAILED DESCRIPTION OF THE INVENTION

Figure 6:
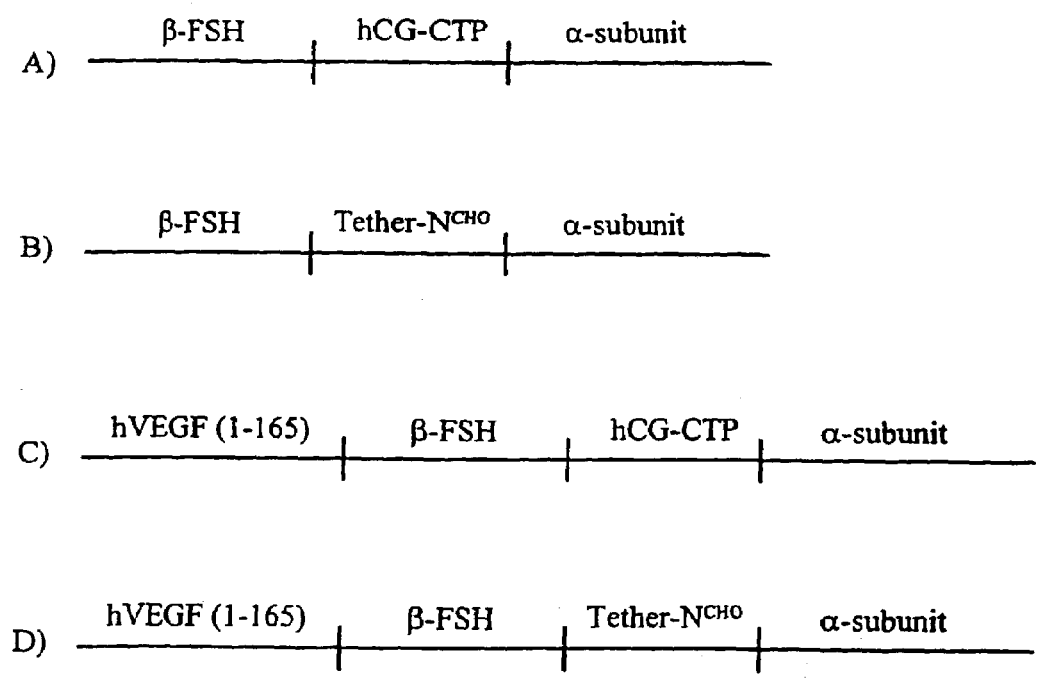
FIG. 6: (Panel A) Schematic rhFSH-CTP construct; (Panel B) Schematic rhFSH-N2/N4 construct.

This invention provides FSH analogues, also referred to herein as "synthetic FSH." These analogues represent a significant advance over known agents for several reasons.

Among these is the fact that these analogues can be expressed as single chain polypeptides having both the α and β subunits of FSH and a polypeptide segment having either O- or N-linked glycosylation sites. These single chain analogues are fully functional hormones that are more easily purified than analogues requiring separate expression and subsequent dimerization of the α and β subunits.

Also, the use of N-linked glycosylation sites in the polypeptide segment offers a number of advantages over the use of an hCG carboxy-terminal peptide sequence alone. Specifically, N-linked glycosylation sites are discreet and well-defined. This permits the facile construction of half-life-increasing moieties having one or more glycosylation sites at predetermined locations along a polypeptide, for example. Glycosylation using N-linked sites permits fine-tuning the half-life and thus the bioactivity of the instant synthetic hormones to meet particular therapeutic needs.

The present invention demonstrates that, contrary to what was expected based on earlier studies with rhFSH-CTP analogs, the addition of multiple N-linked glycosylation sites produces a long-acting FSH protein with enhanced bioactivity.

Definitions

The terms "amino acid," "amino acid residue" or "residue" are used interchangeably herein to refer to an amino acid that is incorporated into a protein, polypeptide or peptide. The amino acid can be, for example, a naturally occurring amino acid or an analog of a natural amino acid that can function in a similar manner as the naturally occurring amino acid.

As used herein, "CTP" means the carboxy-terminal peptide of β-hCG, corresponding to amino acid residues 113–145. This portion of hCG contains multiple O-linked glycosylation sites (see FIG. 14).

The letter "h" is used herein to designate the human isoform of a protein or polypeptide. For example, hFSH means human follicle stimulating hormone. FSH is a pituitary glycoprotein essential for follicular growth as well as spermatogenesis, comprised of a noncovalently linked heterodimer of two peptide subunits, α and β. The β subunit is specific to FSH and thus determines its biological activity, while the α subunit is common to the other members of this glycoprotein family, for example, luteinizing hormone (LH), chorionic gonadotrophin (CG) and thyroid-stimulating hormone (TSH).

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, "serum half-life", abbreviated "$t_{1/2}$", means elimination half-life, i.e., the time at which the serum concentration of an agent has reached one-half its initial or maximum value. The term "increased serum half-life" used herein in reference to a synthetic agent means that the synthetic agent is cleared at a slower rate than either the non-synthetic, endogenous agent or the recombinantly produced version thereof. For example, the $t_{1/2}$ of a synthetic FSH, e.g., hFSH-N2, in a subject would be "increased" if it exceeds the $t_{1/2}$ of either endogenous FSH or recombinantly produced native FSH.

As used herein, "suitable host cells" include, but are not limited to, bacterial cells, yeast cells, fungal cells, insect cells, and mammalian cells. Mammalian cells can be transfected by methods well-known in the art such as calcium phosphate precipitation, electroporation and microinjection.

As used herein, "vector" means any nucleic acid vector known in the art. Such vectors include, but are not limited to, plasmid vectors, cosmid vectors, and bacteriophage vectors.

Units, prefixes and symbols may be denoted in their SI accepted form. Unless otherwise indicated, nucleic acid sequences are written left to right in 5' to 3' orientation and amino acid sequences are written left to right in amino- to carboxy-terminal orientation. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In this invention, administering the instant pharmaceutical composition can be effected or performed using any of the various methods and delivery systems known to those skilled in the art. The administering can be performed, for example, intravenously, orally, via implant, transmucosally, transdermally, intramuscularly, and subcutaneously. In addition, the instant pharmaceutical compositions ideally contain one or more routinely used pharmaceutically acceptable carriers. Such carriers are well known to those skilled in the art. The following delivery systems, which employ a number of routinely used carriers, are only representative of the many embodiments envisioned for administering the instant composition.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone).

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

EMBODIMENTS OF THE INVENTION

This invention provides a first synthetic FSH comprising a β-FSH subunit, an α-FSH subunit and a half-life-increasing moiety, wherein the β-FSH subunit, α-FSH subunit and half-life-increasing moiety are covalently bound.

Half-life increasing moieties include, for example, a peptide containing one or more glycosylation sites. A half-life increasing moiety can also be nonpeptidyl, either in whole or in part, for example, polyethylene glycol.

In one embodiment of the instant invention, the β-FSH subunit and α-FSH subunit are bound to each other via the half-life-increasing moiety, and in a preferred embodiment, the β-FSH subunit, the α-FSH subunit and the polypeptide segment exist within a single polypeptide chain.

In one embodiment of the first synthetic FSH, the β-FSH subunit is bound at its C-terminal end to the N-terminal end of the polypeptide segment, and the polypeptide segment is bound at its C-terminal end to the N-terminal end of the α-FSH subunit. In another embodiment, the α-FSH subunit is bound at its C-terminal end to the N-terminal end of the polypeptide segment, and the polypeptide segment is bound at its C-terminal end to the N-terminal end of the β-FSH subunit. In a further embodiment, the synthetic FSH comprises the N-terminal signal sequence of either the β-FSH or α-FSH subunit.

In yet a further embodiment of the first synthetic FSH, the polypeptide segment comprises the carboxy-terminal portion of the β-hCG subunit. In the preferred embodiment, the carboxy-terminal portion of the β-hCG subunit comprises the amino acid sequence corresponding to positions 113–145 of the β-hCG subunit.

The carboxy-terminal portion of the β-hCG subunit is preferably glycosylated on one or more serine residues, constituting one or more O-linked glycosylation sites. This polypeptide segment can also comprise a region having one or more N-linked glycosylation sites.

As used herein, an "N-linked" glycosylation site includes, without limitation, asn followed by any of X-ser, X-thr and X-cys, wherein X is any amino acid except proline, and glycosylation occurs on the asn residue. In this invention, the amino acid sequence of any polypeptide situated N-terminal to, C-terminal to, or in between two N-linked sites, can be of any content and length needed to suit a particular design requirement.

The instant invention also provides a second synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser (SEQ. ID. NO:16). The polypeptide segment may contain one or multiple copies of the amino acid sequence. In another embodiment, the polypeptide segment comprises the sequence gly-ser-gly-ser-asn-ala-thr-gly-ser-gly-ser-asn-ala-thr-ser-gly-ser (SEQ. ID. NO:17).

In one embodiment of the second synthetic FSH, the β-FSH subunit is bound at its C-terminal end to the N-terminal end of the peptide segment. In another embodiment, the β-FSH subunit is bound at its N-terminal end to the C-terminal end of the polypeptide segment.

This invention also provides a third synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ. ID. NO:16), wherein the β-FSH subunit, α-FSH subunit and polypeptide segment are covalently bound. In another embodiment, the polypeptide segment comprises the sequence gly-ser-gly-ser-asn-ala-thr-gly-ser-gly-ser-asn-ala-thr-ser-gly-ser (SEQ. ID. NO:17).

In one embodiment of third synthetic FSH, the synthetic FSH comprises a β-FSH subunit bound at its C-terminal end to the N-terminal end of the β-FSH subunit. In another embodiment, the synthetic FSH comprises an α-FSH subunit bound at its C-terminal end to the N-terminal end of the polypeptide segment, or a β-FSH subunit bound at its C-terminal end to the N-terminal end of the polypeptide segment. Conversely, the synthetic FSH can comprise an α-FSH subunit bound at its N-terminal end to the C-terminal end of the polypeptide segment, or a β-FSH subunit bound at its N-terminal end to the C-terminal end of the polypeptide segment. In a further embodiment, the β-FSH subunit is bound at its C-terminal end to the N-terminal end of the polypeptide segment, which polypeptide segment is bound at its C-terminal end to the N-terminal end of the α-FSH subunit. In yet a further embodiment, the α-FSH subunit is bound at its C-terminal end to the N-terminal end of the β-FSH subunit. In another embodiment, the α-FSH subunit may be bound at its C-terminal end to the N-terminal end of the polypeptide segment, which polypeptide segment may be bound at its C-terminal end to the N-terminal end of the β-FSH subunit.

In certain embodiments of the instant synthetic FSHs, the glycosylation is either O-linked or N-linked glycosylation. The number of glycosylation sites may be any number, such as one, two, three, four, five, or six sites. In a preferred embodiment, each site is separated from its adjacent site by about six amino acid residues.

In an embodiment of any of the instant synthetic FSHs, the α-FSH subunit (if applicable) and β-FSH subunit are from an animal selected from the group consisting of a primate, a horse, a sheep, a bird, a bovine, a pig, a dog, a cat, and a rodent. In the preferred embodiment, the α-FSH and/or β-FSH subunit is a human subunit. In a further preferred embodiment, the α-FSH subunit (if applicable) and the β-FSH subunit exist within a single polypeptide chain along with the half-life-increasing moiety.

In a further embodiment of any of the instant synthetic FSHs, where the half-life increasing moiety is a polypeptide segment having the amino acid sequence ser-gly-ser-asn-ala-thr-gly-ser-gly-ser-asn-ala-thr-ser-gly-ser (SEQ ID NO:16), the polypeptide segment comprises one or a plurality of the amino acid sequence. In another embodiment, the polypeptide segment comprises the sequence gly-ser-gly-ser-asn-ala-thr-gly-ser-gly-ser-asn-ala-thr-ser-gly-ser (SEQ. ID. NO:17).

This invention also provides a pharmaceutical composition comprising one of the instant synthetic FSHs and a pharmaceutically acceptable carrier.

This invention further provides an article of manufacture comprising (a) the instant pharmaceutical composition, and (b) a label and/or instructions indicating a use of the pharmaceutical composition for the enhancement of fertility, egg production and/or spermatogenesis.

This invention provides nucleic acids encoding the instant synthetic FSH molecules, as well as expression vectors and suitable host cells for expressing said molecules. Examples of vectors include a plasmid, a cosmid, a λ phage and a yeast artificial chromosome, abbreviated "YAC". Any suitable cell system may be used to express the synthetic FSH molecules of the instant invention. For example, synthetic FSHs of the instant invention may be expressed in a bacterial cell or in a eukaryotic cell. In a preferred embodiment, a synthetic FSH is expressed in a Chinese hamster ovary cell, since this cell type provides certain advantageous post-translational protein modifications.

This invention also provides a method for producing a polypeptide that comprises growing a cell, for example a Chinese hamster ovary cell, under conditions permitting expression of the polypeptide encoded by the vector therein, and recovering the polypeptide so expressed. In a preferred embodiment, the vector encoding the polypeptide is transfected into the cells and subcultured under conditions that favor the growth of those cells which have taken up the vector. For example, the vector may contain one or more antibiotic resistance genes. Thus, medium containing the antibiotic will favor the growth of only those cells which have been transfected with the vector.

In a preferred embodiment, the polypeptide contains a signal sequence that targets the polypeptide for excretion from the cell. In a further embodiment, the excreted polypeptide may be collected, purified, and concentrated, for example by affinity chromatography, gel electrophoresis, and vacuum-assisted evaporation.

This invention also provides a method for producing a synthetic FSH, which comprises: (a) co-expressing (i) a nucleic acid which encodes an α-FSH subunit, and (ii) a nucleic acid which encodes a polypeptide comprising a β-FSH subunit and a polypeptide segment comprising the amino acid sequence ser-gly-ser-asn-ala-thr-gly-ser-gly-ser-asn-ala-thr-ser-gly-ser (SEQ ID NO:16), under conditions permitting such co-expression; and recovering the synthetic FSH so produced. In another embodiment, the polypeptide segment comprises the sequence gly-ser-gly-ser-asn-ala-thr-gly-ser-gly-ser-asn-ala-thr-ser-gly-ser (SEQ. ID. NO:17). In an embodiment of the instant invention, the polypeptide segment contains one or multiple copies of the amino acid sequence.

In one embodiment, the β-FSH subunit is bound at its C-terminal end to the N-terminal end of the polypeptide segment, or conversely, the β-FSH subunit is bound at its N-terminal end to the C-terminal end of the polypeptide segment.

This invention also provides a method for increasing a subject's fertility which comprises administering to the subject an amount of any of the instant synthetic FSHs effective to enhance the subject's fertility. Determining a therapeutically effective amount of the instant synthetic FSHs can be done based on animal data using routine computational methods.

In one embodiment, this method is used to enhance the efficiency of in vitro fertilization protocols. For example, a synthetic FSH of the instant invention can enhance the success of in vitro fertilization by stimulating follicular maturation and egg production in the subject.

In a preferred embodiment of the instant invention, the synthetic FSH is administered to the subject less frequently than current methods allow. For example, an FSH of the instant invention may be administered every other day, every 6 to 8 days, or weekly. The instant FSH can also be administered daily.

This invention also provides a method for increasing a subject's egg production which comprises administering to the subject an amount of a synthetic FSH of the instant invention effective to enhance the subject's egg production.

This invention further provides a method for increasing spermatogenesis in a subject through administering to the subject an amount of a synthetic FSH of the instant invention effective to enhance the subject's spermatogenesis.

As used herein, a subject can be, for example, a primate, a horse, a sheep, a bird, a bovine, a pig, a dog, a cat, or a rodent. In the preferred embodiment, the subject is a human.

This invention further provides a method of increasing the half-life of a molecule in a subject, which method comprises glycosylating the molecule in a manner effective to increase the molecule's half-life.

In one embodiment, the molecule is a non-peptidyl organic molecule. In another embodiment, the molecule is a polypeptide. In a further embodiment, the glycosylation is either O-linked or N-linked glycosylation. The number and spacing of glycosylation sites is as set forth herein for the instant synthetic FSHs.

This invention further provides a method for increasing the level of inhibin-A in a subject which comprises administering to the subject an amount the instant synthetic FSH effective to increase the subject's inhibin-A level.

As used herein, "increasing" inhibin A levels includes, for example, increasing inhibin A levels in a subject's bloodstream and/or at specific tissues or organs in the subject, such as the ovaries.

This invention also provides a method for increasing the quality of an oocyte which comprises contacting the oocyte with an amount of the instant synthetic FSH effective to increase the quality of the oocyte.

In one embodiment, the contacting is performed ex vivo. As used herein, the "quality" of an oocyte includes, for example, the ability of the oocyte to produce a viable embryo. The quality of an oocyte also includes, by way of further example, its ability to fuse with a sperm, exit the ovum, implant in the uterus, and undergo cell division.

Finally, this invention provides a method for increasing the quality of an oocyte in a subject which comprises administering to the subject an amount of the instant synthetic FSH effective to increase the quality of the oocyte in the subject.

In the instant methods for increasing inhibin-A levels and increasing oocyte quality, all embodiments of the instant synthetic FSH, subject, and administration set forth for other methods herein are envisioned.

This invention is illustrated in the Experimental Details section which follows. This section is set forth to aid in an understanding of the invention but is not intended to, and should not be construed to, limit in any way the invention as set forth in the claims which follow thereafter.

Experimental Details

The present invention demonstrates the feasibility of generating long-acting, biologically active single-chain hFSH analogues comprising both the α and β subunits. This invention further demonstrates the use of N-linked glycosylation signal sequences to confer a substantially increased half-life to the single-chain recombinant FSH proteins. This invention provides novel, single-chain hFSH analogues consisting of both the α and β subunits of hFSH linked by a peptide tether. The tether comprises either the CTP (the resulting protein designated rhFSH-CTP) or tandem copies of the N-linked glycosylation signal sequence (either two copies, designated rhFSH-N2 or four copies, designated rhFSH-N4). The use of N-linked sites offers the further advantage over the CTP of more precise control over the number of carbohydrates that are introduced into a synthetic peptide. This also provides more versatility in peptide design. Furthermore, in contrast to the attempts to improve the β-hFSH-CTP by adding additional CTP sequences, the addition of multiple tandem repeats of N-linked glycosylation signal sequences produces a hormone with enhanced bioactivity, as demonstrated for the rhFSH-N4 protein in Example 3.

Prior to this invention, the feasibility of creating long-acting, biologically active hFSH by the incorporation of N-linked sequences was doubtful. This is because the N-linked sugars play an important but poorly defined role in gonadotropin-mediated signal transduction. Thus, altering the hormone's repertoire of N-linked sugars was expected to negatively affect its bioactivity. The present invention demonstrates not only that a single-chain hFSH comprising additional N-linked sugars is biologically active, but that the further addition of N-linked moieties produces a hormone with surprising properties, namely an enhanced ability to increase serum inhibin A levels that is unrelated to its longer serum half-life. These FSH analogues are expected to be particularly useful in increasing the efficacy of in vitro fertilization protocols, both in agriculturally important mammals and in humans.

Synopsis

This invention provides synthetic FSHs consisting of single chain fusions of β-hFSH, the common α-subunit, and an additional peptide moiety that provides an increased serum half-life while not interfering with biological activity and even enhancing bioactivity. The pharmacokinetics, pharmacodynamics, and in vivo bioactivity of several examples of these synthetic FSHs in female rhesus monkeys and in rats are presented herein. The results demonstrate that both the absorption and the elimination half-lives of the instant synthetic FSHs are prolonged compared with native recombinant hFSH. Importantly, the analogues tested herein also demonstrated comparable in vitro bioactivity and enhanced in vivo activity compared with native recombinant hFSH.

Figure 7:
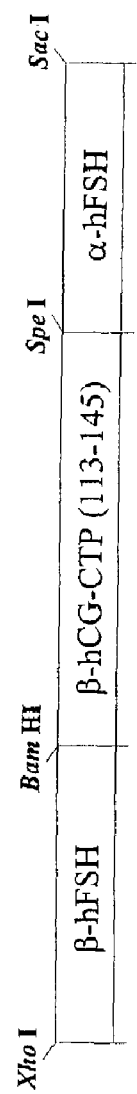
FIG. 7: Schematic of rhFSH-CTP construct with locations of restriction sites.

Five examples of long-lasting FSH analogues are presented herein. The sequences of the fusion proteins β-hFSH-N2 and β-hFSH-N4 are shown in FIGS. 1 and 2, respectively. The sequences of the single-chain FSH analogues, rhFSH-CTP, rhFSH-N2 and rhFSH-N4 are shown in FIGS. 3–5, respectively. Schematics of the CTP and N2/N4 constructs are shown in FIGS. 6 and 7. Detailed in vitro and in vivo bioactivity, as well as pharmacokinetic and pharmacodynamic analyses, were conducted for the single-chain FSH analogues and this data is presented in the section which follows.

Methods

General

Cloning and preparation of plasmid DNA were performed with *E. coli* strain DH5α. Clones were grown in standard Luria-Bertani medium (LB) for purification of recombinant DNA constructs. Transformation of DH5α was performed according to standard techniques using calcium chloride.

All enzymes for recombinant DNA were purchased from New England Biolabs (Beverly, Mass.). The DNA primers for PCR were synthesized by the Columbia Protein Core Laboratory. All products were sequenced to ascertain that no mutations had been erroneously introduced.

PCR reactions were performed with Vent DNA polymerase (New England Biolabs, Beverly, Mass.) and all products of the reactions were sequenced to ensure that no mutations were introduced during the amplification.

Construction of the rhFSH-CTP Fusion Protein

A 5' primer introduced a Xho I site in the same frame and adjacent to the 5' ATG of the β-hFSH cDNA sequence whereas the 3' primer introduced an in frame Bam HI site adjacent to the codon for the last residue of the mature β-FSH which eliminated the terminator codon. In a similar fashion, a cDNA encoding the carboxy-terminal peptide of hCG (residues 113–145 of the hCG β-subunit sequence) was amplified with an in-frame Bam HI site adjacent to the codon for residue 113 and an in-frame Xba I site adjacent to the codon for residue 145. These two fragments were ligated to form a contiguous Xho I-Bam HI-Xba I β-hFSH-CTP fusion without a terminator codon at the 3' end. This fusion was then ligated to a cDNA encoding the mature α-subunit, lacking the amino-terminal signal peptide but including the terminator codon, flanked by in-frame 5' Spe I and 3' Sac I sites. The final construct encodes a fusion of the β-hFSH and α-subunit with the CTP sequence as the linker sequence. This final fusion sequence was then inserted into an SV40 expression vector.

Construction of the rhFSH-N2 and -N4 Fusion Proteins

The rhFSH-N2 and -N4 constructs consist of a single polypeptide chain hFSH molcule containing the β- and α-subunits tethered by a synthetic polypeptide consisting of either one or two tandem copies of the following: Ser-Gly-Ser-Asn-Ala-Thr-Gly-Ser-Gly-Ser-Asn-Ala-Thr-Ser-Gly-Ser (SEQ. ID. NO:16). β-hFSH-N2 was constructed by synthesizing two complementary DNA strands encoding the above polypeptide in one of six potential reading frames. These two DNAs were designed such that following annealing, a 5' Bam HI end and a 3' Spe I end were formed. The synthetic DNA duplex was then ligated into a vector with the hFSH β- and α-subunit encoding cDNAs. The in-frame ligation of these three DNAs was accomplished by placing a Xho I site immediately preceding the start codon and replacing the terminator codon of the hFSH β-subunit with a Bam HI site. In addition, an Spe I site was placed at the 5' end and a Sac I immediately following the terminator codon of the α-subunit. The three fragments were then inserted into an SV40-based expression vector at Xho I/Sac I sites to form the β-hFSH-N2 expression construct. To insert a second copy of the synthetic polypeptide, a Bgl II site was inserted at the end of the synthetic sequence in the β-hFSH-N2 clone immediately preceding the Spe I site. The second copy of the synthetic polypeptide was then inserted by cleaving the β-hFSH-N2 construct with Bgl II and Spe I followed by an insertion of the Bam HI/Spe I ended synthetic DNA to form β-hFSHN4. This was feasible since Bam HI and Bgl II have identical cohesive termini.

Construction of the rhFSH-N4 Fusion Protein

The rhFSH-N2 construct was used as a template for generating the rhFSH-N4 construct. A digest was set up with Xho/Spe I which liberated the β-FSH-N2 sequence, while leaving the α-subunit in the SV40 vector with a 5' Spe I sticky end. The β-FSH-N2 part was then amplified using PCR technology with 5' Xho and 3' Bgl II sticky ends. The synthetic oligopeptide with 5' Bam HI and 3' Spe I sticky ends, used for making the hFSH-N2, was inserted.

Expression of rhFSH Fusion Proteins

An SV40 expression clone containing the fusion construct was co-transfected into Chinese hamster ovary cells (CHO-K1) along with an SV2neo clone encoding resistance to the antibiotic G418. The CHO cell transformation was performed using a standard calcium phosphate precipitate technique. Selectable media containing G418 (Gemini Bioproducts, Woodland, Calif.) was used to select transfected cells. Isolated colonies were pooled and maintained in Ham's F-12 culture medium containing 500 ug/mL G418, 10% fetal bovine serum, 100 units/mL penicillin, 100 ug/mL streptomycin, and 4 mM glutamine. Pooled colonies were subcloned in 96 well microtiter dishes and clones were isolated that secreted, for example, about 3 pmole/mL of the fusion protein (rhFSH-CTP). To obtain higher yields, cells were grown in suspension cultures, which produced, for example, about 9–14 pmole/mL (rhFSH-CTP).

Purification of rhFSH Fusion Proteins

Spinner bottles were seeded at $10^5$ cells/mL in CHO-S-SFM medium (Life technologies, Rockville, Md.) containing 400 ug/mL G418. Cultures generally reached a density of $2 \times 10^6$ cells/mL on day 6 or 7, and the cell supernatant was harvested on day 7 or 8. PMSF was added to the supernatant at a concentration of 0.2 mM, which was then filtered through a 0.2 μm membrane and stored at 4° C. Affinity purification of was accomplished using an α-subunit specific antibody column. The column was prepared by coupling purified α-subunit specific immunoglobulins to CNBr-Sepharose-4B according to the manufacturer's instructions (Amersham Pharmacia Biotech, Piscataway, N.J.) at a concentration of 5 mg antibody/mL Sepharose. After applying the cell supernatant, the column was washed with 50 bed volumes of PBS followed by 2 bed volumes of distilled water. The fusion protein was eluted with 3–4 bed volumes of 1 M acetic acid and immediately dried on a Speed-Vac concentrator (Savant Instruments, Holbrook, N.Y.).

Expression and Purification of rhFSH-N4

An SV40 expression clone containing the construct was cotransfected into CHO-K1 cells with an SV2neo clone encoding resistance to. G418, using Lipofectamine Plus™ (Invitrogen Life Technologies, Carlsbad, Calif.). To isolate the clones, media containing G418 (Gemini Bioproducts, Woodland, Calif.) was used. The isolate clones were pooled and maintained in Ham's F12 containing 500 μg/ml G418, 10% fetal bovine serum, 100 units/ml penicillin, 100 μg/ml streptomycin and 4 mM glutamine. Production of the pooled cells was assessed by an anti-β FSH RIA (Biodesign International, Saco, Me.). To further increase production, cells were grown in suspension cultures, with spinner bottles seeded at $10^5$ cells/ml in CHO-S-SFM II (Life Technologies, Rockville, Md.) containing 400 μg/ml G418. On day 6 or 7 usually a density of $2 \times 10^6$ cells/ml was reached and the cell supernatant was harvested on day 7 or 8. Supernatants received 0.2 mM PMSF and were filtered through a 0.2 mm membrane and kept at 4° C. until the day of purification. Purification was performed as described in Klein et al., 2003. The pooled CHO cells were producing 0.19 pmole hFSH-N4. When grown in suspension culture, production was increased to 1.3 pmole/ml.

In vitro FSH Bioactivity

Bioactivity of the hFSH analogues was evaluated using Y-1 cells transfected with the FSH receptor. Y-1 cell cultures were mixed with the fusion protein and native pituitary hFSH (control) at varying concentrations and media was assayed for cAMP activity as described in Lindau-Shepard et al., 2001.

Alternatively, for the experiments described in Examples 2 and 3, receptor binding was assessed using CHO cells expressing the FSH receptor (CHO-FSHR) on their surface as previously described (Kelton et al., 1992). Cell cultures were mixed with rhFSH-N4, rhFSH-N2, rhFSH-CTP and rhFSH at varying concentrations. Media was assayed for cAMP using a cAMP radioimmunoassay kit (PerkinElmer, Boston, Mass.).

Subcutaneous Protocol for Example 1

Rhesus monkeys were injected subcutaneously with the fusion protein (n=4) or rhFSH (Follistim, Organon Inc., n=2) at a dose of 10 IU/kg. All except 1 of the monkeys in each of the two treatment groups had been ovariectomized prior to injection. Serum hFSH was assayed prior to injection and at the following intervals post-injection: 12 h, 16 h, 20 h, 24 h, 36 h, 48 h, 60 h, and every 24 hours thereafter until levels reached baseline (approximately 9 days for control animals, 19–22 days for treatment animals).

Intravenous (IV) Protocol

One rhesus monkey was given an IV bolus of the fusion protein (10 IU/kg). A second animal was given an IV bolus of the control, rhFSH at the same dose. Serum was assayed for hFSH prior to bolus administration and at the following intervals post-injection: 0.5 h, 1 h, 2 h, 4 h, 8 h, 12 h, 24 h, 36 h, 48 h, 72 h, 96 h, 120 h, 144 h and 168 h.

Pharmacokinetics

Recombinant human FSH (rhFSH) (Follistim, Organon Inc, West Orange, N.J.) was used as a control. The Immulite assay (Diagnostic Products Corporation, Los Angeles, Calif.) was used to quantitate hFSH protein. This assay was able to detect the hFSH analogues in vitro and in vivo, and did not cross-react with rhesus FSH.

Pharmacokinetic Analysis

Each individual data set was evaluated by the pharmacokinetic data analysis program PKAnalyst (Micromath, Inc., Salt Lake City, Utah). For the IV dosing study, the following biexponential equation was fitted to the data: $C(t) = Ae^{-at} + Be^{-bt}$, where C(t) is the plasma concentration at time "t", and A and B are the multiexponential coefficients. Values of a and b represent the initial-phase disposition rate constant and the terminal-phase disposition rate constant, respectively. PKAnalyst was used to generate the best-fit critical pharmacokinetic parameters, including elimination rate constant, half-life of initial (distribution) phase ($t_{1/2a}$), half-life of terminal (elimination) phase ($t_{1/2b}$), and total area under the blood concentration-time curve (AUC).

For the subcutaneous dosing studies, the blood concentration-time data were represented by the following biexponential equation: $C(t)=A(e^{-Ket}-e^{-Kat})$ where $C(t)$ is the blood concentration at time "t" and A the multiexponential coefficient. Ke and Ka represent the elimination rate constant and absorption rate constant, respectively. All parameter estimates were computed by PKAnalyst. Bioavailability of rhFSH and the hFSH analogues were estimated from the ratio of AUC (SC)/AUC (IV), at a constant dose (10 IU/kg).

In vivo FSH Bioactivity

Ganirelix Acetate (250 μg) was administered by SC injection for 10 consecutive days to two normally cycling Rhesus monkeys beginning menstrual cycle day 4. The hFSH analogue was administered as a single subcutaneous dose (10 IU/kg) on cycle day 6. Venipuncture was performed daily and serum assayed for estradiol levels from cycle day 2 through cycle day 14. Serum estradiol was measured using an automated Immulite assay (Diagnostic Products Corporation, Los Angeles, Calif.).

Alternatively, hypophysectomized mice (surgery at 19 days) were purchased from the Charles River Company (Wilmington, Mass.). Upon arrival, mice were rehydrated with glucose-supplemented water for four days and randomized into control and experimental groups. Control recombinant hFSH protein or hFSH analogue was administered via a single subcutaneous injection in a total volume of 100 microliters at a dose of 10 IU. On day four post-injection, the animals were weighed and sacrificed by carbon dioxide asphyxiation followed by cardiopuncture and drainage. The uterus and ovaries were weighed and sectioned for histologic analysis.

Histologic Preparation and Follicle Counts

Both ovaries were removed from each animal. One ovary was weighed, immersed in formalin for fixation and embedded in paraffin according to standard protocols. Sections were cut at four to five micron intervals and every tenth section was stained with hematoxylin and eosin. Follicle density and maturation were assessed using the method of Pedersen and Peters (1968).

Mass Spectrophotometry Analyses for Example 3

Samples were purified by reverse phase chromatography HPLC (Hewlett-Packard 1090) Vydac C4 column to remove any carrier proteins or other minor impurities. 25% of the HPLC fractions containing the peaks of interest were dried in a Speed-Vac and redissolved in 3 μl of saturated solution of α-cyano-4-hydroxycinnamic acid in 1:2:3 formic/propanol/water. A small aliquot (0.5 μl) was spotted on a sample plate prepared with a thin layer of α-cyano-4-hydroxycinnamic acid for mass spectrometric analyses. Using a PerSeptive Biosystems Voyager-DE RP MALDI mass spectrometer, peaks were observed for our constructs.

Electrophoresis and Western Blotting for Example 3

SDS-PAGE was performed and proteins were transferred to nitrocellulose using standard techniques (Laemmli, 1970; Towbin et al., 1979; Burnette, 1981). After blocking, the nitrocellulose was incubated overnight in a 1:10,000 dilution of a monoclonal antibody to FSH-β from Biodesign International (Saco, Me.). The membrane was then washed and incubated for 1 hour in a 1:10,000 dilution of a peroxidase conjugated polyclonal antibody to mouse immunoglobulins (Amersham-Pharmacia Biotech, Piscataway, N.J.). After washing, the nitrocellulose was incubated in a chemiluminescent detection reagent according to the manufacturer's directions (Amersham Pharmacia). Bands were visualized by exposure to X-ray film.

Isoelectric Focusing Gel Electrophoresis for Example 3

Samples were electrophoresed on a Novex pre-cast IEF gel, with a pI range of pH 3 to pH 7 according to manufacturer's instructions (Invitrogen, Carlsbad, Calif.) and then visualized by silver staining.

In vivo Bioactivity for Examples 2 and 3

Immature, 21 day old female Sprague Dawley (SD) rats were obtained from Charles River Laboratories (Wilmington, Mass.). They were housed three to a cage and given standard food and tap water ad libitum. Animals were randomly assigned to one of 4 treatment groups: single chain rhFSH-CTP, rhFSH, rhFSH-N2 or rhFSH-N4, n=3 (Example 2) or n=5 (Example 3) for each group. At 23 days old a single IV dose of 2800 ng/rat (42 IU) of hormone was given via dorsal tail vein. Serum was obtained by periorbital venipuncture at the following intervals post-injection: 0.5 hrs, 1 hrs, 3 hrs, 6 hrs, 12 hrs and 24 hrs. Prior to injection and each bleed, anesthesia with isoflorane was administered by inhalation. At 48 hours post-injection rats were euthanized by carbon dioxide inhalation followed by exsanguination via cardiac puncture. Ovaries were then extirpated and weighed. Serum at 48 hrs was assayed for inhibin A using an inhibin A kit (Oxford Bio-Innovations, Oxfordshire, England).

Pharmacokinetic Analysis for Example 3

Animals were randomly assigned to one of 4 treatment groups: single chain rhFSH-CTP, rhFSH, rhFSH-N2 or rhFSH-N4, n=5 for each group. At 23 days old a single ip dose of 2800 ng/rat of hormone was given. Serum was obtained by venipuncture via dorsal tail vein at the following intervals post-injection: 3 hrs, 6 hrs, 9 hrs, 12 hrs, 24 hrs, 30 hrs and 74 hrs. Prior to injection and each bleed, anesthesia with isoflorane was administered by inhalation. Pharmacokinetic analysis was performed using PK Solutions 2.0 software (Summit Research Services, Montrose, Colo.). Pharmacokinetic parameters were determined for each rat for terminal (elimination) half-life ($t_{1/2}$) and area under the serum concentration-time curve (AUC). Clearance (Cl) was calculated using the relationship Cl=Dose/AUC.

EXAMPLE 1

The rhFSH-CTP Fusion Protein

In vitro Bioactivity

Figure 8:
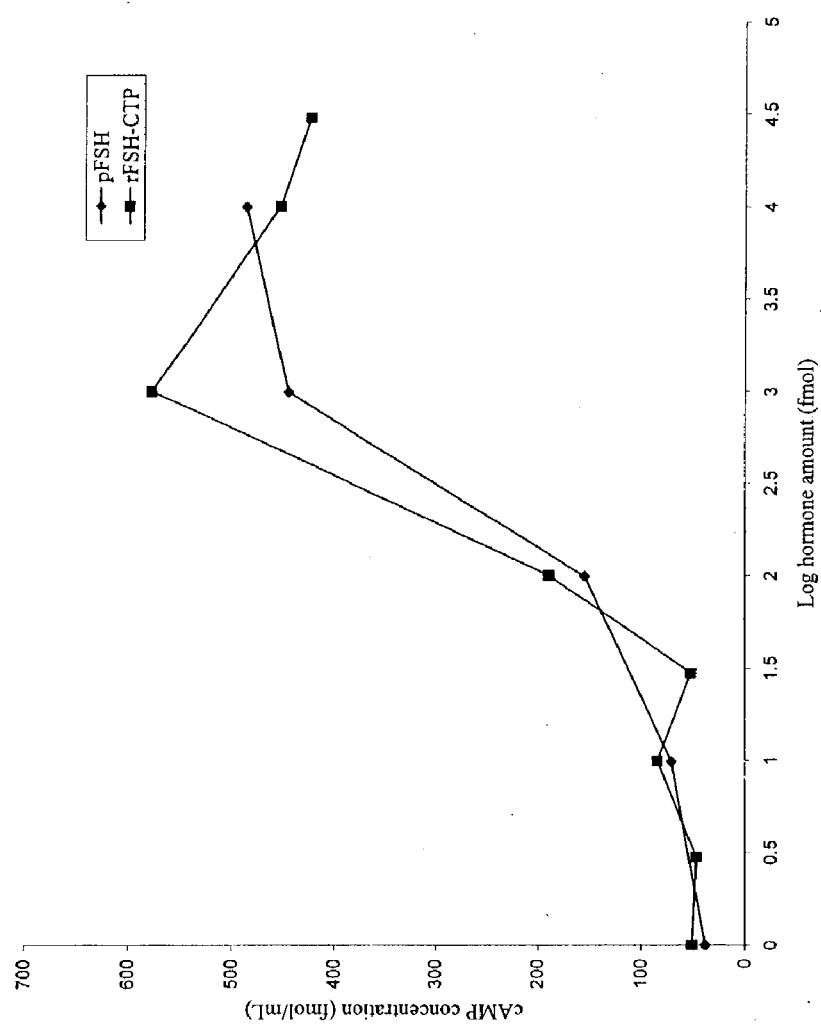
FIG. 8: In vitro bioassay of hormone activity. cAMP concentration (fmol/ml) was quantitated in Y1 cells expressing the FSH receptor after treatment with the indicated amount of either pituitary FSH (rhFSH) or the FSH analogue, rhFSH-CTP.

The bioactivity of the rhFSH-CTP analogue was first assessed by an assay of hFSH receptor activity. In this assay, a recombinant native hFSH receptor is expressed in a suitable host cell and cAMP induction is measured following incubation with hormone (Lindau-Shepard et al., 2001). As shown in FIG. 8, the rhFSH-CTP analogue induced a similar rise in cAMP levels when compared with recombinant hFSH, demonstrating that this single-chain fusion analogue folded properly into an unhindered, biologically active hormone.

Pharmacokinetics

In order to establish the pharmacokinetic parameters of the instant synthetic FSH, Rhesus monkeys were injected with an IV bolus dose (10 IU/kg) of either a recombinant native hFSH, or the rhFSH-CTP analogue. The serum concentration of hFSH was determined by immunoassay at times following injection and a serum concentration-time curve was generated based on the data. For both the recombinant native hFSH and the rhFSH-CTP analogue, the resulting curve fit a two-compartment model, consisting of an initial distribution half-life and a second, slower, elimination half-life. As indicated by the pharmacokinetic parameter estimates listed in Table 1, the half-life of elimination for the rhFSH-CTP analogue was more than four-fold longer than that of the native hFSH.

TABLE 1

Pharmacokinetic parameter estimates after IV bolus injection of rhFSH-CTP or the control recombinant hFSH protein (rhFSH), each at a dose of 10 IU/kg. AUC = area under the curve.

| PARAMETER | rhFSH-CTP | rhFSH |
| --- | --- | --- |
| $T_{1/2\ distribution}$ (hr) | 3.16 | 1.39 |
| $T_{1/2\ elimination}$ (hr) | 35.29 | 8.25 |
| AUC (mIU/ml d) | 278 | 38.8 |
| Clearance (1/kg hr) | 1.5 | 10.74 |

Figure 9:
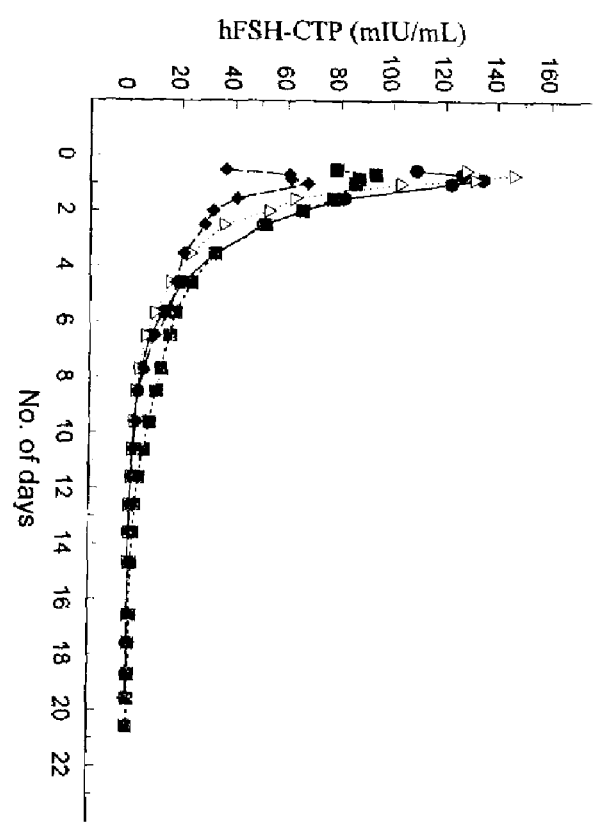
FIG. 9: Serum levels of the FSH analogue, rhFSH-CTP, in 4 rhesus monkeys (indicated by triangles, inverted triangles, circles, and squares, respectively) measured at the indicated times following a single subcutaneous injection at a dose of 10 IU/kg.
Figure 10:
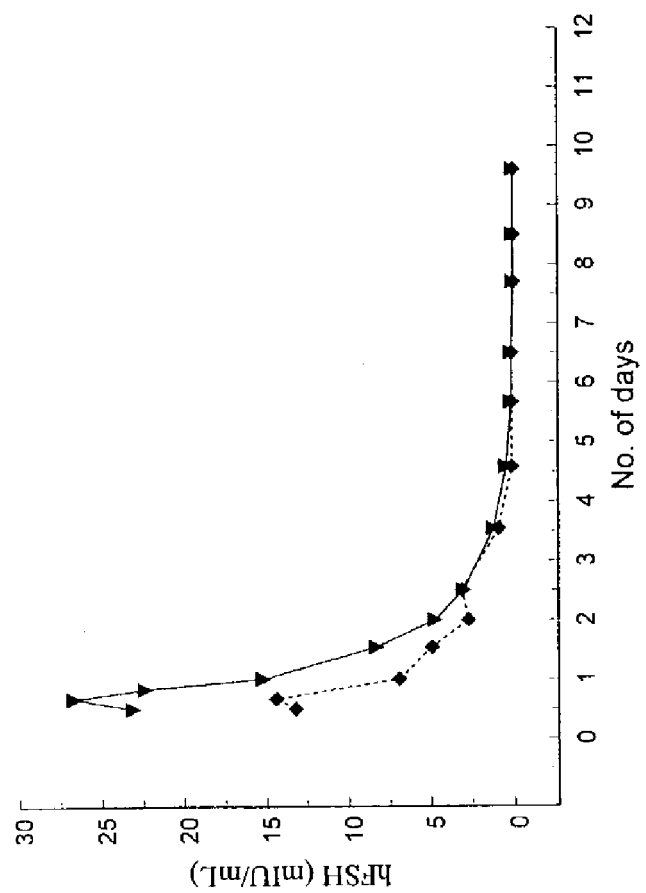
FIG. 10: Serum levels of the control protein, rhFSH, in 2 rhesus monkeys (indicated by diamonds and triangles, respectively) measured at the indicated times following a single subcutaneous injection at a dose of 10 IU/kg.

Although these results obtained following an intravenous bolus injection were encouraging, it was also important to determine the pharmacokinetic parameters of the synthetic FSH following a subcutaneous injection. This is because subcutaneous administration is a relatively easier route for clinical use. As indicated by the serum concentration-time curves for treatment animals (n=4) receiving the rhFSH-CTP analogue (FIG. 9) versus controls (n=2) receiving native rhFSH (FIG. 10), the serum levels of native rhFSH approached baseline by day 4 post-injection, whereas elevated (>2 mIU/mL) levels of the rhFSH-CTP analogue were maintained for approximately 10 days. These data fit a one-compartment pharmacokinetic model, the parameter estimates of which are given in Table 2.

TABLE 2

Mean pharmacokinetic parameter estimates after subcutaneous injection of rhFSH-CTP (n = 4) or the control, rhFSH (n = 2), each at a dose of 10 IU/kg. Bioavailability was calculated as AUCsc/AUCiv. AUC = area under the curve.

| PARAMETER | rhFSH-CTP | rhFSH |
| --- | --- | --- |
| $T_{1/2\ elimination}$ (hr) | 35.23 | 15.74 |
| $T_{1/2\ absorption}$ (hr) | 5.04 | 1.75 |
| $C_{max}$ (mIU/ml) | 101.26 | 25.77 |
| $T_{max}$ (hr) | 16.39 | 5.95 |
| AUG (mIU/ml d) | 275.31 | 30.96 |
| Bioavailability (%) | 99 | 80 |

Notably, the half-life of absorption for the instant synthetic FSH was approximately threefold longer than that of the native hFSH. These results show that the half-life of elimination correlates well with the intravenous data and confirms the slower metabolism and clearance of the rhFSH-CTP analogue. Addition of the CTP moiety to hFSH thus induced a depot effect, retarding the absorption of the product following subcutaneous administration. This explains the slower time to reach peak concentration ($t_{max}$) for animals receiving the rhFSH-CTP analogue. As indicated in Table 2, both drugs were highly bioavailable after subcutaneous administration.

In vivo Bioactivity

Figure 11:
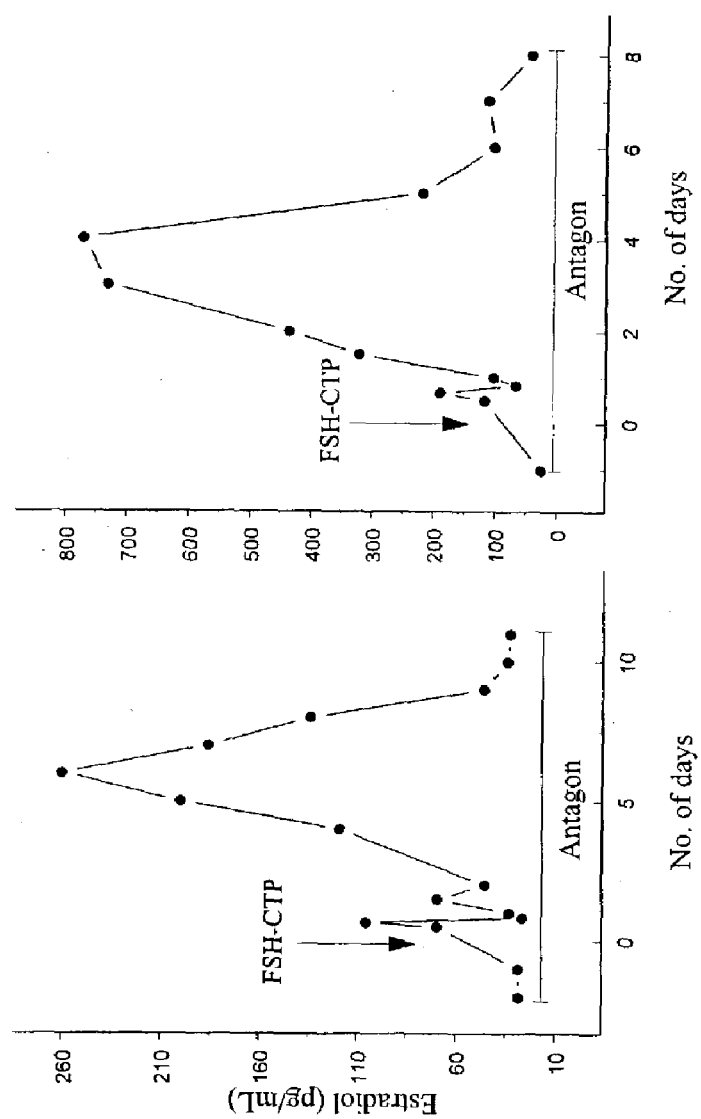
FIG. 11: Serum estradiol levels in two normally cycling monkeys following a single subcutaneous injection of the FSH analogue, rhFSH-CTP. The time of injection is indicated by arrows. Both monkeys were given the GnRH antagonist Ganirelix Acetate for the duration of the study.

To establish the bioactivity of the rhFSH-CTP analogue in vivo, two normally cycling monkeys were injected with a single dose of the analogue, and serum was assayed for estradiol at various times following injection. Both monkeys were given a GnRH antagonist (Antagon, Organon, West Orange, N.J.) for the duration of the study, eliminating any effect on ovarian estrogen production from endogenous Rhesus FSH. As shown in FIG. 11, serum estradiol levels initially increased in both animals, with peak levels achieved at 3 and 5 days post-injection. One monkey attained supraphysiologic levels of estradiol (peak 773 pg/mL) on day 4 post-injection, suggesting early recruitment of multiple follicles. Thus, the rhFSH-CTP analogue demonstrated similar, and in one case substantially increased, in vivo biological activity compared to native hFSH.

CONCLUSIONS

The results presented herein demonstrate that a single chain FSH comprising both the β and α subunits of hFSH with an intervening CTP retained the ability to bind and activate the FSH receptor. Furthermore, the fusion protein was metabolized at a slower rate than the native hormone, as circulating levels remained elevated for an extended period of time compared to native recombinant hFSH. Quantitatively, the half-life of elimination for the rhFSH-CTP analogue following subcutaneous administration was 2 to 3 times longer than that of native recombinant hFSH. This difference corresponds well with the only previous report on pharmacokinetics in humans, which was done with male subjects, in which the half-life of elimination after subcutaneous administration was prolonged by a similar magnitude compared with historic controls receiving native hormone.

These results also confirm the accuracy of our parameter estimate for elimination half-life by assessing pharmacokinetics after IV administration. Surprisingly, absorption of the rhFSH-CTP analogue was delayed by approximately three-fold following subcutaneous administration. The long circulating presence of the rhFSH-CTP analogue after subcutaneous administration is thus explained not only by a decreased metabolism of the protein, but by a depot effect resulting in slower absorption.

In summary, the pharmacodynamics and biological activity of a rhFSH-CTP analogue in a primate model are described herein for the first time. Administration of the rhFSH-CTP analogue to 2 monkeys given a GnRH antagonist (to suppress endogenous FSH activity) elicited a dramatic rise in serum estradiol levels. A single subcutaneous dose resulted in elevated estradiol levels for 5–7 days, with one monkey achieving a peak estradiol level greater than 3 times that seen during a normal endogenous Rhesus cycle. This supraphysiologic response is indicative of multifollicular recruitment, although sonographic confirmation was not performed. Such prolonged elevations in estradiol are not normally seen after isolated subcutaneous injections of native recombinant hFSH.

These results confirm the feasibility of achieving prolonged ovarian stimulation following a single injection of a recombinant gonadotropin analogue. Fewer injections will result in less patient discomfort, improved compliance, and possibly a reduction in the number of local side effects.

Combination therapy using both long and short-acting FSH formulations, either together and/or sequentially during a stimulation cycle, should also be considered. In these cases, the short-acting (native) formulation may be used to "fine-tune" the FSH dose after an initial bolus of a long-acting analog.

Ideal candidates for treatment with long-acting FSH analogues include infertile males with hypogonadotropic hypogonadism, who typically require prolonged courses of gonadotropin therapy. This technology also provides a significant improvement over current methods for stimulating follicular maturation and egg production in a subject being treated for infertility and for in vitro fertilization protocols.

EXAMPLE 2

The rhFSH-N2 Fusion Protein

In vitro Bioactivity

Figure 17:
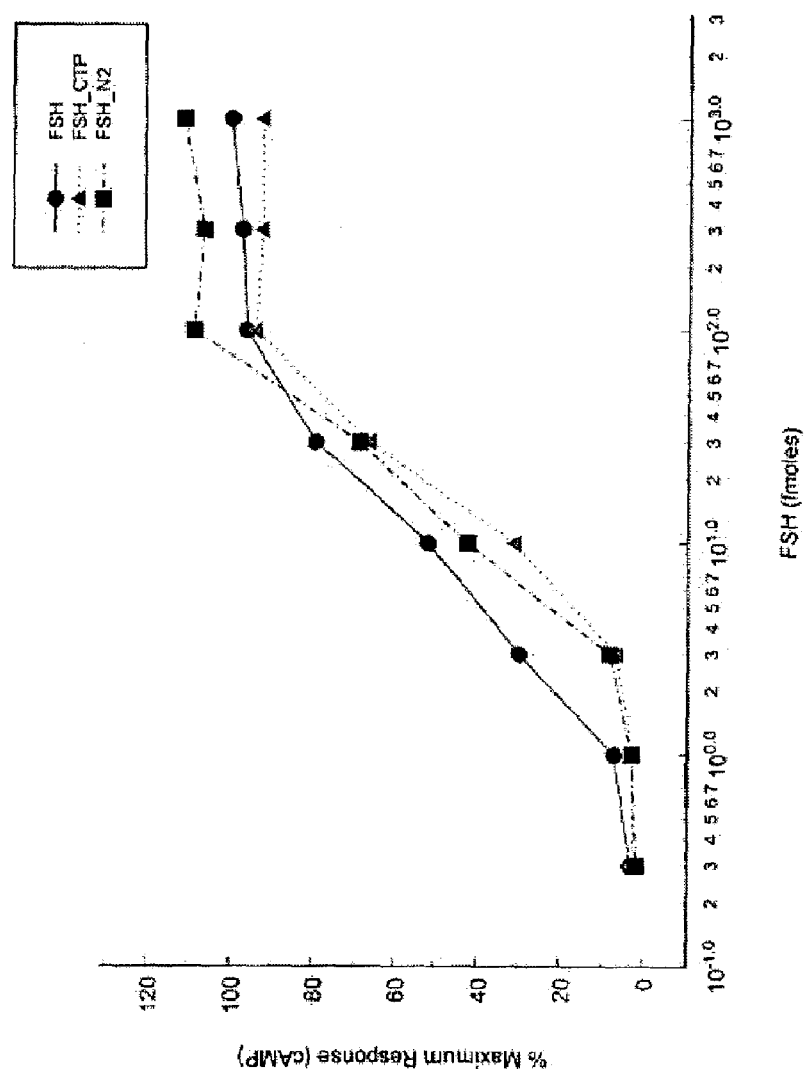
FIG. 17: In vitro bioactivity as assessed by induction of cAMP in CHO cells expressing the FSH receptor for the indicated FSH analogue. Maximum response corresponds to the highest level of cAMP induced by rhFSH in $2\times10^4$ cells (approximately 3000–5000 fmol cAMP)

The bioactivity of rhFSH-N2 was first assessed using an assay that measures cAMP induction as an indicator of FSH receptor activation. As shown in FIG. 17, the cAMP induction mediated by the rhFSH-N2 analogue was comparable to that achieved with either native rhFSH or rhFSH-CTP, demonstrating that the rhFSH-N2 analogue retains the same bioactivity as rhFSH and rhFSH-CTP. Thus, like the CTP analogue discussed above, this single-chain fusion protein folded properly into an unhindered, biologically active hormone.

Pharmacokinetics

Figure 18:
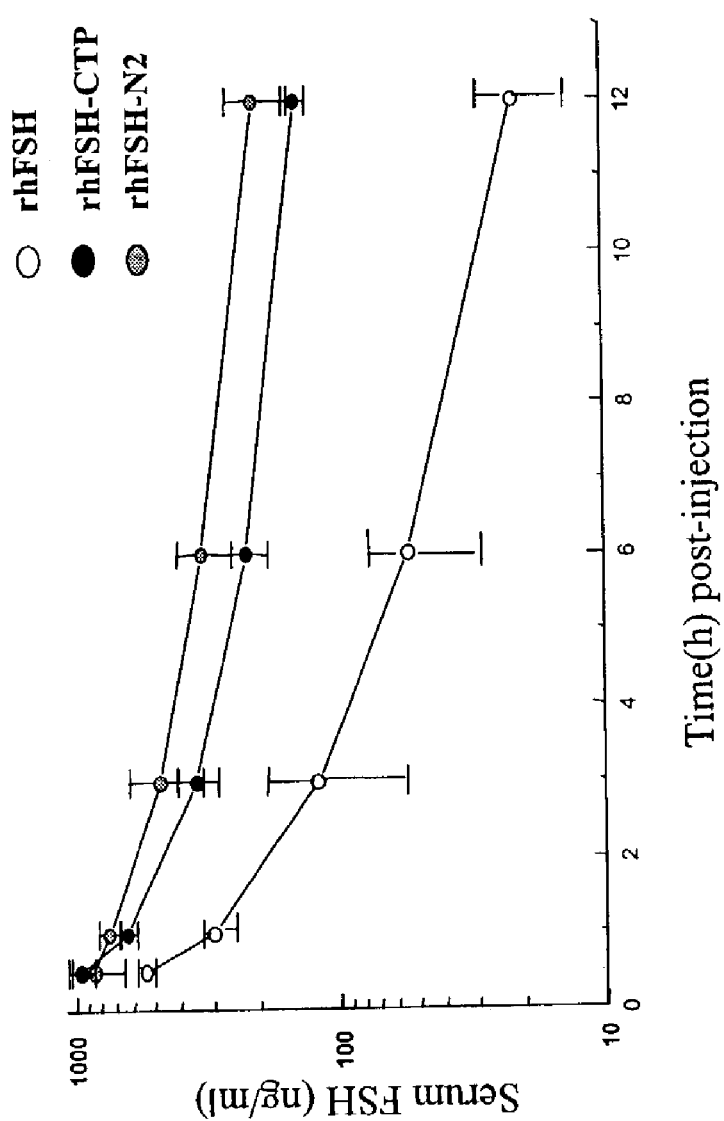
FIG. 18: Nucleotide (SEQ. ID. NO:14) and amino acid sequence (SEQ. ID. NO:15) of α-hFSH. The signal sequence corresponds to the sequence beginning with the methionine at position 1 and ending with the serine at position 24.

Pharmacokinetic analysis was performed using twelve immature female rats divided into four groups of 3 each. Each of the three proteins (hFSH, hFSH-CTP, hFSH-N2) was diluted to 11 μg/ml in injection buffer containing BSA (1 mg/ml), and given as a single intravenous dose of 2800 ng/rat in 0.25 ml of buffer. The control group received 0.25 ml of saline (data not shown). Serum was assayed at the following intervals post-injection: 0.5, 1.0, 3.0, 6.0, and 12 hours. The serum concentration-time curves are shown in FIG. 18. For all products the curves could be explained by a two-compartment model, with an initial half-life reflecting the distribution phase, and a second, slower elimination half-life. As indicated by the pharmacokinetic parameter estimates in Table 3, The elimination half-life of rhFSH-N2 (7.3 hr) was comparable with that of rhFSH-CTP (7.1 hr) and approximately 2-fold longer than rhFSH (3.7 hr).

TABLE 3

Mean pharmacokinetic parameter estimates after IV bolus injection of rhFSH, rhFSH-CTP or hFSH-N2, each at a dose of 2800 ng/rat (n = 3). AUC = area under the curve.

| PARAMETER | rhFSH | rhFSH-CTP | rhFSH-N2 |
|---|---|---|---|
| $AUC_{0-infinity}$ (ng/hr/ml) | 1491 | 3887 | 4802 |
| $T_{1/2\ elimination}$ (hr) | 3.7 | 7.1 | 7.3 |
| Clearance (ml/hr) | 1.9 | 0.72 | 0.58 |

As shown in Table 4, the amount of hormone present in the circulation at all time-points post-injection was significantly higher for rhFSH-N2 compared with rhFSH. Mean plasma levels of rhFSH-N2 were not significantly different from those of rats receiving rhFSH-CTP, although p-values were near the usual significance for later time points (0.057 and 0.062 for time-points 6 and 12 hr, respectively).

TABLE 4

Comparison of mean serum concentrations of rats receiving rhFSH-N2 to those receiving either rhFSH or rhFSH-CTP at all time points post-i.v. injection of hormone (2800 ng). Significance is indicated (calculated using one-way layout with Bonferroni corrections for multiple comparisons, each time period considered as a separate analysis.

| Time (hr) | rhFSH-N2 ng/ml Mean +/− SD | rhFSH ng/ml Mean +/− SD | p | rhFSH-CTP ng/ml Mean +/− SD | p |
|---|---|---|---|---|---|
| 0.5 | 845 +/− 187.8 | 540 +/− 40.1 | 0.053 | 958.8 +/− 111 | ns |
| 1 | 747 +/− 73.2 | 299.2 +/− 36 | 0.00012 | 635.8 +/− 51 | ns |
| 3 | 467 +/− 129 | 119.1 +/− 77 | 0.0074 | 343.5 +/− 55.6 | ns |
| 6 | 324 +/− 65 | 53.6 +/− 21 | 0.00059 | 220 +/− 34.1 | 0.057 |
| 12 | 198 +/− 42 | 21.2 +/− 7.1 | 0.0036 | 137.7 +/− 14.6 | 0.062 |

In vivo Bioactivity

Figure 19A:
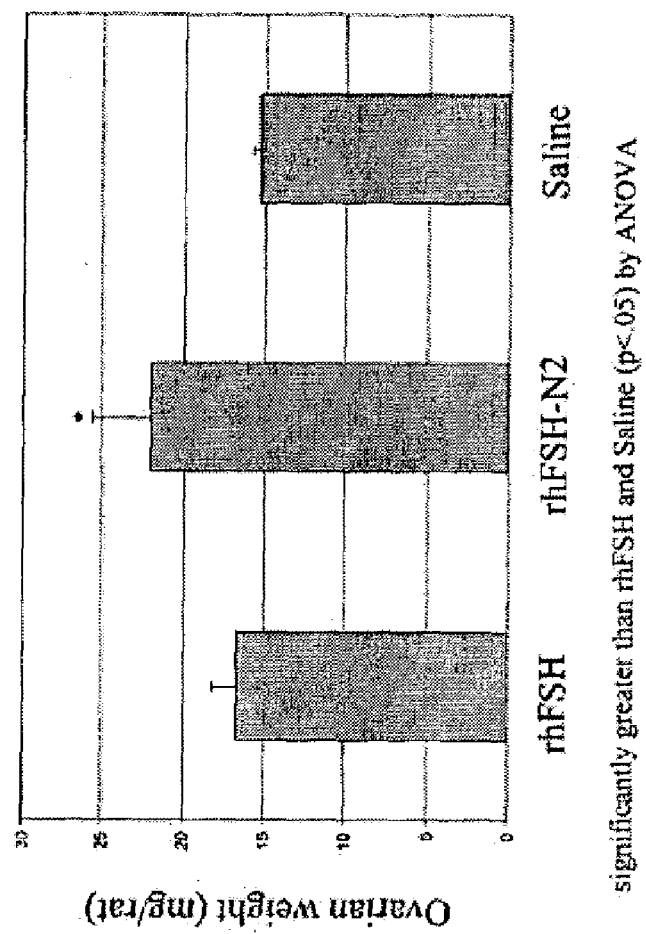
FIG. 19: Mean ovarian weight three days following subcutaneous injection of 21 day old female rats with either recombinant human FSH (rhFSH), rhFSH-N2, or saline, Panel A; rhFSH-CTP or rhFSH-N2, Panel B; rhFSH, rhFSH-CTP, rhFSH-N2 or rhFSH-N4, Panel C (n=3 rats for each group).
Figure 19B:
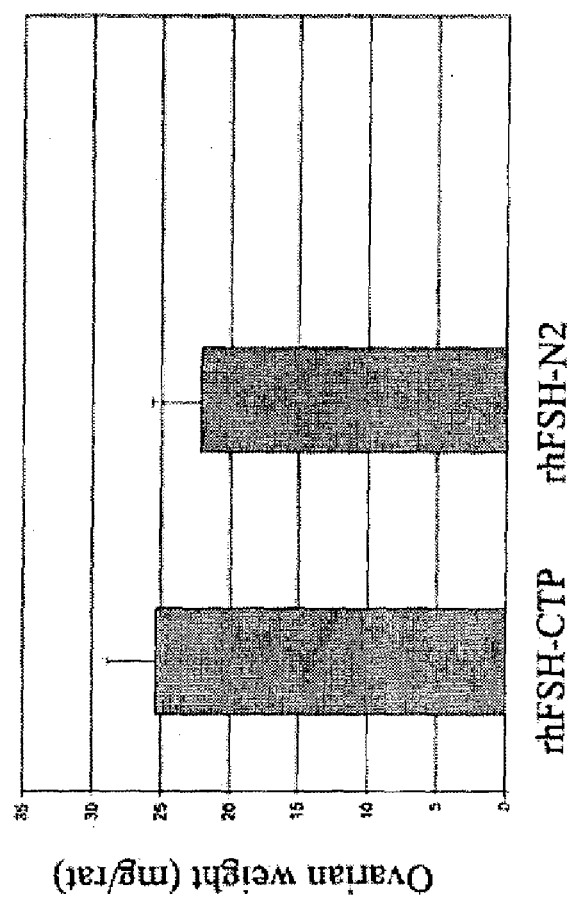

An ovarian weight gain assay was used to assess the in vivo bioactivity of rhFSH-N2 relative to that of rhFSH and the rhFSH-CTP. Mean ovarian weights following a single subcutaneous injection of either saline, rhFSH, or rhFSH-N2 are shown in FIG. 19A. The results of the simultaneous contrast testing indicated significant differences in the mean log ovarian weight in animals receiving rhFSH-N2 as compared with those receiving rhFSH (p<0.025). There was no significant difference between the ovarian weights of rats receiving rhFSH-N2 and rhFSH-CTP (FIG. 19B).

CONCLUSIONS

The results described herein demonstrate that the addition of N-linked carbohydrates imparts a longer half-life to native hFSH, thereby increasing its bioactivity in a manner analogous to that conferred by the O-linked sugars on the CTP.

These results further demonstrate that a synthetic sequence bearing artificial N-linked glycosylation consensus sequences can be efficiently glycosylated in cultured cells. This in turn demonstrates the feasibility of producing synthetic FSH having improved stability and bioactivity through directed modifications of glycosylation patterns via the addition of artificial sequences.

EXAMPLE 3

The rhFSH-N4 Fusion Protein

An important component of in vitro fertilization protocols is the injection of FSH, a pituitary hormone that is important for follicular development in the ovaries (Macklon et al., 2001). During the late phase of follicular development, following FSH stimulation, a dominant follicle emerges and increased levels of the hormones estrogen and inhibin are detectable. There are two isoforms of inhibin, designated A and B. The induction of inhibin is a useful biomarker for ovarian function. Inhibin B is associated with follicular development while inhibin A correlates with follicular maturation (Hall et al., 1999; Groome et al., 1994).

This example describes a novel single-chain synthetic FSH, rhFSH-N4, with a surprising ability to elevate the serum levels of inhibin A. The magnitude of the increase in serum inhibin A was considerably greater than that obtained with either rhFSH or rhFSH-CTP.

Biochemical Analyses

Purified rhFSH-N4 had a molecular weight of approximately 64,000 daltons, as determined by SDS gel electrophoresis and Western blotting. Under the same conditions, rhFSH-N2 and rhFSH-CTP had molecular weights of approximately 58,000 and 53,000, respectively. This is lower than the expected increase in mass for rhFSH-N4 due to increased glycosylation relative to rhFSH-N2 and rhFSH-CTP.

Isoelectric focusing gel electrophoresis demonstrated that rhFSH-CTP and rhFSH-N4 each have a more acidic profile than rhFSH, consistent with the prediction that the CTP and rhFSH-N4 analogs have higher levels of glycosylation. Five major isoforms of rhFSH were evident between pI 4.65–4.1. For rhFSH-N4, discrete bands were present between 4.65–3.8, with a smear of bands continuing to a pI of 3.0.

The carbohydrate component of the fusion proteins, rhFSH, rhFSH-N2, and rhFSH-N4, was more directly analyzed by MALDI mass spectrometry. Peaks corresponded with masses of 14,034 ($\alpha$-subunit) and 16,569 ($\beta$-subunit) daltons for rhFSH, and 36,971, 38,514, and 40,925 daltons for hFSH-CTP, hFSH-N2, and hFSH-N4, respectively. The carbohydrate component was determined by subtracting the calculated peptide mass (sum of the molecular weights of the constituent amino acids) from the peptide mass determined by MALDI mass spectrometry, yielding 8,575 for rhFSH, 15,077 for rhFSH-N2, and 15,501 for rhFSH-N4. These results indicated that the carbohydrate content of the rhFSH-N4 analog was lower than expected, relative to that of the rhFSH-N2 analog. Thus, the glycosylation of the rhFSH-N4 analog is likely to be incomplete.

In vitro Bioactivity

The ability of the rhFSH-N4 analog to bind to and activate the FSH receptor was examined using the assay described in Example 2. In this assay, cAMP is used as an indicator of FSH receptor binding and activation in CHO-K1 cells. cAMP was measured following exposure of the cells to various concentrations of rhFSH and each fusion protein (hFSH-CTP, hFSH-N2, and hFSH-N4). The results indicated no significant difference in the ability of the proteins to induce FSH receptor activity (data not shown).

Pharmacokinetics

Mean pharmacokinetic parameters were determined following a single i.p. injection of 2800 ng/animal (n=5/group) of rhFSH or one of the fusion proteins: rhFSH-CTP, rhFSH, rhFSH-N2 or hFSH-N4, as described in Methods. The data is summarized in Table 5. The elimination half-life of hFSH-rhFSH-N4 (13.67 hr) was increased over that obtained with the other two fusion proteins rhFSH-N2 and rhFSH-CTP, which were similar to each other (12.258 hr and 12.056 hr, respectively). Each of the fusion proteins had a half-life significantly greater than that of rhFSH (6.25 hr) ($p < 0.05$).

TABLE 5

Mean pharmacokinetic parameter estimates after i.p. injection of rhFSH, rhFSH-CTP, rhFSH-N2, or rhFSH-N4, each at a dose of 2800 ng/rat (n = 5)

| PARAMETER | rhFSH | rhFSH-CTP | rhFSH-N2 | rhFSH-N4 |
|---|---|---|---|---|
| $AUC_{0-infinity}$ (ng/hr/ml) | 812 | 2408 | 3512 | 3896 |
| $T_{1/2\ elimination}$ (hr) | 6.25 | 12.06 | 12.26 | 13.67 |
| Clearance (ml/hr) | 3.51 | 1.217 | 0.8132 | 0.7391 |

In vivo Bioactivity

Figure 19C:
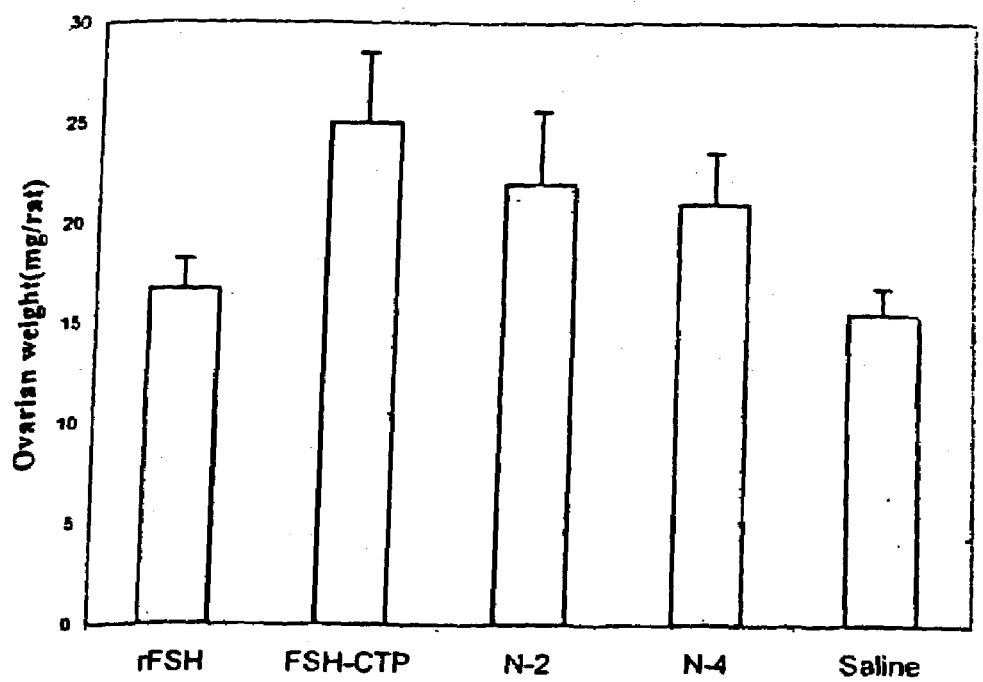

The relative in vivo bioactivity of the rhFSH and the rhFSH-CTP, rhFSH-N2, and rhFSH-N4 fusion proteins was first assessed using an ovarian weight gain assay. Each analogue was administered in a single subcutaneous injection to each of three rats and the ovarian weights were determined at 48 hrs post-injection. As shown in FIG. 19C, the weight gains for the single-chain fusion proteins, rhFSH-N4, rhFSH-N2, and rhFSH-CTP were comparable, while all were significantly higher than rhFSH ($p < 0.05$).

In addition to the ovarian weight gain assay, mean levels of inhibin A at 48 hours post-injection were examined as an indicator of bioactivity, and ovarian function in particular. As shown in Table 6, each of the fusion proteins elicited increased serum levels of inhibin A relative to that obtained with rhFSH ($p < 0.05$). Surprisingly, the mean inhibin A levels achieved with rhFSH-N4 were substantially greater than those obtained with either rhFSH-CTP or rhFSH-N2. The latter exhibited approximately a 2-fold increase in inhibin A over that obtained with rhFSH, while rhFSH-N4 elicited inhibin A levels that were over 6-fold greater than those obtained with rhFSH. This effect on inhibin A is unlikely to be the result of increased hormone stability alone, since rhFSH-N4 also elicited inhibin A levels that were almost three-fold higher than those obtained with rhFSH-CTP and rhFSH-N2.

TABLE 6

Serum inhibin A (ng/ml) at 48 hr for rats (22 days old) injected with either saline or 2800 ng/rat of the indicated FSH analogue (n = 3).

| | saline | rhFSH | rhFSH-CTP | rhFSH-N2 | rhFSH-N4 |
|---|---|---|---|---|---|
| MEAN: | 25.5 | 92.4 | 223.0 | 222.2 | 617.8 |

Discussion

This Example describes a novel FSH fusion protein, designated rhFSH-N4, that exhibits a surprising and unexpected biopotency, namely, the ability to induce relatively high levels of serum inhibin A. Compared to rhFSH, which is the recombinant FSH used in most in vitro fertilization protocols, rhFSH-N4 increased serum inhibin A by over 6-fold. Furthermore, rhFSH-N4 demonstrated an enhanced ability to increase inhibin A over that obtained with either rhFSH-N2 or rhFSH-CTP. This is particularly surprising because rhFSH-N4 did not differ substantially from rhFSH-N2 or rhFSH-CTP in either serum half-life or bioactivity as measured in an ovarian weight gain assay.

Inhibins B and A are important in follicular development and maturation, respectively. Following stimulation with rhFSH, inhibin A in rats does not increase until the late follicular phase, indicating its secretion by the dominant follicle. Thus, inhibin A is likely to promote improved oocyte quality for in vitro fertilization protocols. Accordingly, the rhFSH-N4 described herein is expected to provide an advantage over existing recombinant forms of FSH, including rhFSH-CTP and rhFSH-N2, by promoting oocyte quality through increased inhibin A.

The surprising biopotency of the rhFSH-N4 protein in the inhibin A assay is unlikely to be solely a result of its increased circulating half-life, which is comparable among all three fusion proteins. Instead, it may be related to an alteration in the carbohydrate content of the rhFSH-N4 protein. Although the rhFSH-N4 protein comprises twice the number of N-linked glycosylation sites as the rhFSH-N2 protein, its carbohydrate mass was only slightly higher, as determined by mass spectrometry (MALDI). Steric hindrance may have prevented full sialylation of the carbohydrate chains or may have caused the formation of alternately branched carbohydrate chains.

The internal structure of the carbohydrate chains of FSH proteins also affects their bioactivity. Proteins containing biantennary, truncated, and hybrid-type oligosaccharides show a higher bioactivity, whereas highly branched carbohydrate structures are associated with lower bioactivity (Creus et al., 2001). Since the molecular weight of the four added carbohydrate chains of rhFSH-N4 was comparable to the two added chains of rhFSH-N2, the carbohydrate chains of rhFSH-N2 are likely to be longer and more highly branched, perhaps contributing to its decreased bioactivity in the inhibin A assay compared to rhFSH-N4.

REFERENCES

Baird, D. T. (2001) Is there a place for different isoforms of FSH in clinical medicine? IV. The clinician's point of view. Hum Reprod. 16:1316–1318.

Burnette W. N. (1981) "Western Blotting": electrophoretic transfer of proteins from sodium dodecyl sulfate-polyacrylamide gels to unmolded nitrocellulose and radiologic detection with antibody and radioiodinated protein A. Anal Biochem, 112:195–203

Bouloux, P. M., D. J. Handelsman, F. Jockenhovel, E. Nieschlag, J. Rabinovici, W. L. Frasa, J. J. de Bie, G. Voortman, and J. Itskovitz-Eldor (2001) First human exposure to FSH-CTP in hypogonadotrophic hypogonadal males. Hum. Reprod. 16, 1592–1597.

Calvo, F. O., H. T. Keutmann, E. R. Bergert, and R. J. Ryan (1986) Deglycosylated human follitropin: characterization and effects on adenosine cyclic 3',5'-phosphate production in porcine granulosa cells. Biochemistry 25, 3938–3943.

Creus S., Chaia Z., Pellizzari E. H., Cigorraga S. B., Ulloa-Aguirre A., Campo S. (2001) Human FSH isoforms: carbohydrate complexity as determinant of in-vitro bioactivity. Mol Cell Endocrinol. 174:41–49.

Duijkers I. J., Klipping C., Boerrigter P. J., Machielsen C. S., De Bie J. J., Voortman C. (2002) Single dose pharmacokinetics and effects on follicular growth and serum hormones of a long-acting recombinant FSH preparation (FSH-CTP) in healthy pituitary-suppressed females. Hum Reprod 17:1987–1983.

Fares, F. A., N. Suganuma, K. Nishimori, P. S. Lapolt, A. J. Hsueh, and I. Boime (1992) Design of a long-acting follitropin agonist by fusing the C-terminal sequence of the chorionic gonadotropin beta subunit to the follitropin beta subunit. Proc. Natl. Acad. Sci. U.S.A. 89, 4304–4308.

Feng, W., M. M. Matzuk, K. Mountjoy, E. Bedows, R. W. Ruddon, and I. Boime (1995) The asparagine-linked oligosaccharides of the human chorionic gonadotropin beta subunit facilitate correct disulfide bond pairing. J. Biol. Chem. 270, 11851–11859.

Groome N. P., Illingworth P. J., O'Brien M. et al., (1994) Detection of dimeric inhibin throughout the human menstrual cycle. J clin endocrinol metab 81: 1401–1405.

Hall J. E., Welt C. K., Cramer D. W. (1999) Inhibin A and inhibin B reflect ovarian function in assisted reproduction but are less useful at predicting outcome. Hum Reprod 14: 409–415.

Kelton C. A., Cheng S. V., Nugent N. P., Schweickhardt R. L., Rosenthal J. L., Overton S. A., Wands G. D., Kuzeja J. B., Luchette C. A., Chappel S. C. (1992) The cloning of the human follicle stimulating hormone receptor and its expression in COS-7, CHO, and Y-1 cells. Mol Cell.

Klein J., Lobel L., Pollak S., Ferin M., Xiao E., Sauer M. V., Lustbader J. W. (2002) Pharmacokinetics and pharmacodynamics of single-chain recombinant human follicle stimulating hormone containing the human chorionic gonadotropin carboxyterminal peptide in the rhesus monkey. Fertil Steril 77: 1248–1255.

Krichevsky, A., S. Birken, J. F. O'Connor, K. Bikel, J. Schlatterer, and R. E. Canfield (1994) The development of a panel of monoclonal antibodies to human luteinizing hormone and its application to immunological mapping and two-site assays. Endocrine 2, 511–520.

Laemmli U. K. (1970) Cleavage of structural proteins during the assembly of the head of bacteriophage T4. Nature, 227:680–5.

LaPolt P. S., Nishimori K., Fares F. A., Perlas E., Boime I. and Hsueh A. J. W. (1992) Design of a long-acting follitropin agonist by fusing the C-terminal sequence of the chorionic gonadotropin beta subunit to the follitropin beta subunit. Proc Natl Acad Sci USA 89 4304–4308.

LeContonnec, J. Y., H. C. Porchet, V. Beltrami, A. Khan, S. Toon, and M. Rowland (1994) Clinical pharmacology of recombinant human follicle-stimulating hormone. II. Single doses and steady-state pharmacokinetics. Fertil. Steril. 61, 679–86.

Lindau-Shepard, B. A., H. A. Brumberg, A. J. Peterson, and J. A. Dias (2001) Reversible immunoneutralization of human follitropin receptor. J. Reprod. Immun. 49, 1–19.

Macklon N. S., Fauser B. C. (2001) Follicle-stimulating hormone and advanced follicle development in the human. Arch Med Res 32:595–600.

Matzuk, M. M., A. J. Hsueh, P. Lapolt, A. Tsafriri, J. L. Keene, and I. Boime (1990) The biological role of the carboxyl-terminal extension of human chorionic gonadotropin beta-subunit. Endocrinology 126, 376–383.

Pedersen, T. and H. Peters (1968) Proposal for a classification of oocytes and follicles in the mouse ovary. J. Reprod. Fertil 17, 555–557.

Pierce, J. G. and T. F. Parsons (1981) Glycoprotein hormones: structure and function. Annu. Rev. Biochem. 50, 465–495.

Porchet, H. C., J. Y. LeContonnec, B. Neuteboom, S. Canali, and G. Zanolo (1995) Pharmacokinetics of recombinant human luteinizing hormone. J. Clin. Endocrinol. Metab. 80, 667–73.

Sairam, M. R. and P. Manjunath (1982) Studies on pituitary follitropin. XL Induction of hormonal antagonistic activity by chemical deglycosylation. Mol. Cell Endocrinol. 28, 139–150.

Saal, W., H. J. Glowania, and J. Happ (1991) Pharmacodynamics and pharmacokinetics after subcutaneous and intramuscular injection of human chorionic gonadotropin. Fertil. Steril. 56, 225–8.

Suganuma, N., M. M. Matzuk, and I. Boime (1989) Elimination of disulfide bonds affects assembly and secretion of the human chorionic gonadotropin beta subunit. J. Biol. Chem. 264, 19302–19307.

Towbin H., Staehelin T., Gordon J. (1979) Electrophoretic transfer of proteins from polyacrylamide gels to nitrocellulose sheets: procedure and some applications. Proc Natl Acad Sci USA, 76:4350–4.

Yen, S. S., O. Llerena, B. Little, and O. H. Pearson (1968) Disappearance rates of endogenous luteinizing hormone and chorionic gonadotropin in man. J. Clin. Endocrinol. Metab 28, 1763–1767.

SEQUENCE LISTING

<160> NUMBER OF SEQ ID NOS: 17

<210> SEQ ID NO 1
<211> LENGTH: 441
<212> TYPE: DNA
<213> ORGANISM: human
<220> FEATURE:
<221> NAME/KEY: CDS
<222> LOCATION: (1)..(438)

<400> SEQUENCE: 1

```
atg aag aca ctc cag ttt ttc ttc ctt ttc tgt tgc tgg aaa gca atc        48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa        96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc       144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa       192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga       240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg       288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt       336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa       384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca       432
Glu Gly Ser Gly Ser Asn Ala Thr Gly Ser Gly Ser Asn Ala Thr Ser
    130                 135                 140 gga tcc taa                                                            441
Gly Ser
145
```

<210> SEQ ID NO 2
<211> LENGTH: 146
<212> TYPE: PRT
<213> ORGANISM: human

<400> SEQUENCE: 2

```
Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
```

```
                      85                  90                  95
Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu Gly Ser Gly Ser Asn Ala Thr Gly Ser Gly Ser Asn Ala Thr Ser
        130                 135                 140

Gly Ser
145

<210> SEQ ID NO 3
<211> LENGTH: 486
<212> TYPE: DNA
<213> ORGANISM: human
<220> FEATURE:
<221> NAME/KEY: CDS
<222> LOCATION: (1)..(483)

<400> SEQUENCE: 3 atg aag aca ctc cag ttt ttc ttc ctt ttc tgt tgc tgg aaa gca atc       48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa       96
Cys Cys Asn Ser Cys Glu Leu Thr Asn Ile Thr Ile Ala Ile Glu Lys
                20                  25                  30 gaa gaa tgt cgt ttc tgc ata agc atc aac acc act tgg tgt gct ggc      144
Glu Glu Cys Arg Phe Cys Ile Ser Ile Asn Thr Thr Trp Cys Ala Gly
            35                  40                  45 tac tgc tac acc agg gat ctg gtg tat aag gac cca gcc agg ccc aaa      192
Tyr Cys Tyr Thr Arg Asp Leu Val Tyr Lys Asp Pro Ala Arg Pro Lys
        50                  55                  60 atc cag aaa aca tgt acc ttc aag gaa ctg gta tat gaa aca gtg aga      240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg      288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt      336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa      384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca      432
Glu Gly Ser Gly Ser Asn Ala Thr Gly Ser Gly Ser Asn Ala Thr Ser
    130                 135                 140 aga tcc gga tcg aac gcg acg ggg tca ggt tct aat gca act tca gga      480
Arg Ser Gly Ser Asn Ala Thr Gly Ser Gly Ser Asn Ala Thr Ser Gly
145                 150                 155                 160 tcc taa                                                              486
Ser

<210> SEQ ID NO 4
<211> LENGTH: 161
<212> TYPE: PRT
<213> ORGANISM: human

<400> SEQUENCE: 4

Met Lys Thr Leu Gln Phe Phe Phe Leu Phe Cys Cys Trp Lys Ala Ile
1               5                   10                  15
```

```
Cys Cys Asn Ser Cys Glu Leu Thr Asn Ile Thr Ile Ala Ile Glu Lys
         20                  25                  30

Glu Glu Cys Arg Phe Cys Ile Ser Ile Asn Thr Thr Trp Cys Ala Gly
         35                  40                  45

Tyr Cys Tyr Thr Arg Asp Leu Val Tyr Lys Asp Pro Ala Arg Pro Lys
 50                  55                  60

Ile Gln Lys Thr Cys Thr Phe Lys Glu Leu Val Tyr Glu Thr Val Arg
 65                  70                  75                  80

Val Pro Gly Cys Ala His His Ala Asp Ser Leu Tyr Thr Tyr Pro Val
             85                  90                  95

Ala Thr Gln Cys His Cys Gly Lys Cys Asp Ser Asp Ser Thr Asp Cys
             100                 105                 110

Thr Val Arg Gly Leu Gly Pro Ser Tyr Cys Ser Phe Gly Glu Met Lys
             115                 120                 125

Glu Gly Ser Gly Ser Asn Ala Thr Gly Ser Gly Ser Asn Ala Thr Ser
             130                 135                 140

Arg Ser Gly Ser Asn Ala Thr Gly Ser Gly Ser Asn Ala Thr Ser Gly
 145                 150                 155                 160

Ser
```

<210> SEQ ID NO 5
<211> LENGTH: 777
<212> TYPE: DNA
<213> ORGANISM: human
<220> FEATURE:
<221> NAME/KEY: CDS
<222> LOCATION: (1)..(774)

<400> SEQUENCE: 5

```
atg aag aca ctc cag ttt ttc ttc ctt ttc tgt tgc tgg aaa gca atc      48
Met Lys Thr Leu Gln Phe Phe Phe Leu Phe Cys Cys Trp Lys Ala Ile
 1               5                  10                  15 tgc tgc aat agc tgt gag ctg acc aac atc acc att gca ata gag aaa      96
Cys Cys Asn Ser Cys Glu Leu Thr Asn Ile Thr Ile Ala Ile Glu Lys
             20                  25                  30 gaa gaa tgt cgt ttc tgc ata agc atc aac acc act tgg tgt gct ggc     144
Glu Glu Cys Arg Phe Cys Ile Ser Ile Asn Thr Thr Trp Cys Ala Gly
         35                  40                  45 tac tgc tac acc agg gat ctg gtg tat aag gac cca gcc agg ccc aaa     192
Tyr Cys Tyr Thr Arg Asp Leu Val Tyr Lys Asp Pro Ala Arg Pro Lys
 50                  55                  60 atc cag aaa aca tgt acc ttc aag gaa ctg gta tat gaa aca gtg aga     240
Ile Gln Lys Thr Cys Thr Phe Lys Glu Leu Val Tyr Glu Thr Val Arg
 65                  70                  75                  80 gtg ccc ggc tgt gct cac cat gca gat tcc ttg tat aca tac cca gtg     288
Val Pro Gly Cys Ala His His Ala Asp Ser Leu Tyr Thr Tyr Pro Val
             85                  90                  95 gcc acc cag tgt cac tgt ggc aag tgt gac agc gac agc act gat tgt     336
Ala Thr Gln Cys His Cys Gly Lys Cys Asp Ser Asp Ser Thr Asp Cys
             100                 105                 110 act gtg cga ggc ctg ggg ccc agc tac tgc tcc ttt ggt gaa atg aaa     384
Thr Val Arg Gly Leu Gly Pro Ser Tyr Cys Ser Phe Gly Glu Met Lys
             115                 120                 125 gaa gga tcc ccc cgc ttc cag gac tcc tct tcc tca aag gcc cct ccc     432
Glu Gly Ser Pro Arg Phe Gln Asp Ser Ser Ser Ser Lys Ala Pro Pro
             130                 135                 140 ccc agc ctt cca agc cca tcc cga ctc ccg ggg ccc tcg gac acc ccg     480
Pro Ser Leu Pro Ser Pro Ser Arg Leu Pro Gly Pro Ser Asp Thr Pro
 145                 150                 155                 160
```

-continued

```
atc ctc cca caa act agt gct cct gat gtg cag gat tgc cca gaa tgc      528
Ile Leu Pro Gln Thr Ser Ala Pro Asp Val Gln Asp Cys Pro Glu Cys
            165                 170                 175 acg cta cag gaa aac cca ttc ttc tcc cag ccg ggt gcc cca ata ctt      576
Thr Leu Gln Glu Asn Pro Phe Phe Ser Gln Pro Gly Ala Pro Ile Leu
            180                 185                 190 cag tgc atg ggc tgc tgc ttc tct aga gca tat ccc act cca cta agg      624
Gln Cys Met Gly Cys Cys Phe Ser Arg Ala Tyr Pro Thr Pro Leu Arg
            195                 200                 205 tcc aag aag acg atg ttg gtc caa aag aac gtc acc tca gag tcc act      672
Ser Lys Lys Thr Met Leu Val Gln Lys Asn Val Thr Ser Glu Ser Thr
    210                 215                 220 tgc tgt gta gct aaa tca tat aac agg gtc aca gta atg ggg ggt ttc      720
Cys Cys Val Ala Lys Ser Tyr Asn Arg Val Thr Val Met Gly Gly Phe
225                 230                 235                 240 aaa gtg gag aac cac acg gcg tgc cac tgc agt act tgt tat tat cac      768
Lys Val Glu Asn His Thr Ala Cys His Cys Ser Thr Cys Tyr Tyr His
                245                 250                 255 aaa tct taa                                                          777
Lys Ser
```

<210> SEQ ID NO 6
<211> LENGTH: 258
<212> TYPE: PRT
<213> ORGANISM: human

<400> SEQUENCE: 6

```
Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu Gly Ser Pro Arg Phe Gln Asp Ser Ser Ser Lys Ala Pro Pro
    130                 135                 140

Pro Ser Leu Pro Ser Pro Ser Arg Leu Pro Gly Pro Ser Asp Thr Pro
145                 150                 155                 160

Ile Leu Pro Gln Thr Ser Ala Pro Asp Val Gln Asp Cys Pro Glu Cys
                165                 170                 175

Thr Leu Gln Glu Asn Pro Phe Phe Ser Gln Pro Gly Ala Pro Ile Leu
            180                 185                 190

Gln Cys Met Gly Cys Cys Phe Ser Arg Ala Tyr Pro Thr Pro Leu Arg
        195                 200                 205

Ser Lys Lys Thr Met Leu Val Gln Lys Asn Val Thr Ser Glu Ser Thr
    210                 215                 220

Cys Cys Val Ala Lys Ser Tyr Asn Arg Val Thr Val Met Gly Gly Phe
```

```
                    225                 230                 235                 240
Lys Val Glu Asn His Thr Ala Cys His Cys Ser Thr Cys Tyr Tyr His
                245                 250                 255
Lys Ser

<210> SEQ ID NO 7
<211> LENGTH: 723
<212> TYPE: DNA
<213> ORGANISM: human
<220> FEATURE:
<221> NAME/KEY: CDS
<222> LOCATION: (1)..(720)

<400> SEQUENCE: 7 atg aag aca ctc cag ttt ttc ttc ctt ttc tgt tgc tgg aaa gca atc      48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa      96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc     144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa     192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga     240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg     288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt     336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa     384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca     432
Glu Gly Ser Gly Ser Asn Ala Thr Gly Ser Gly Ser Asn Ala Thr Ser
    130                 135                 140 gga tcc act agt gct cct gat gtg cag gat tgc cca gaa tgc acg cta     480
Gly Ser Thr Ser Ala Pro Asp Val Gln Asp Cys Pro Glu Cys Thr Leu
145                 150                 155                 160 cag gaa aac cca ttc ttc tcc cag ccg ggt gcc cca ata ctt cag tgc     528
Gln Glu Asn Pro Phe Phe Ser Gln Pro Gly Ala Pro Ile Leu Gln Cys
                165                 170                 175 atg ggc tgc tgc ttc tct aga gca tat ccc act cca cta agg tcc aag     576
Met Gly Cys Cys Phe Ser Arg Ala Tyr Pro Thr Pro Leu Arg Ser Lys
            180                 185                 190 aag acg atg ttg gtc caa aag aac gtc acc tca gag tcc act tgc tgt     624
Lys Thr Met Leu Val Gln Lys Asn Val Thr Ser Glu Ser Thr Cys Cys
        195                 200                 205 gta gct aaa tca tat aac agg gtc aca gta atg ggg ggt ttc aaa gtg     672
Val Ala Lys Ser Tyr Asn Arg Val Thr Val Met Gly Gly Phe Lys Val
    210                 215                 220 gag aac cac acg gcg tgc cac tgc agt act tgt tat tat cac aaa tct     720
Glu Asn His Thr Ala Cys His Cys Ser Thr Cys Tyr Tyr His Lys Ser
225                 230                 235                 240 taa                                                                 723
```

<210> SEQ ID NO 8
<211> LENGTH: 240
<212> TYPE: PRT
<213> ORGANISM: human

<400> SEQUENCE: 8

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu Gly Ser Gly Ser Asn Ala Thr Gly Ser Gly Ser Asn Ala Thr Ser
130                 135                 140

Gly Ser Thr Ser Ala Pro Asp Val Gln Asp Cys Pro Glu Cys Thr Leu
145                 150                 155                 160

Gln Glu Asn Pro Phe Phe Ser Gln Pro Gly Ala Pro Ile Leu Gln Cys
                165                 170                 175

Met Gly Cys Cys Phe Ser Arg Ala Tyr Pro Thr Pro Leu Arg Ser Lys
            180                 185                 190

Lys Thr Met Leu Val Gln Lys Asn Val Thr Ser Glu Ser Thr Cys Cys
        195                 200                 205

Val Ala Lys Ser Tyr Asn Arg Val Thr Val Met Gly Gly Phe Lys Val
210                 215                 220

Glu Asn His Thr Ala Cys His Cys Ser Thr Cys Tyr Tyr His Lys Ser
225                 230                 235                 240

<210> SEQ ID NO 9
<211> LENGTH: 768
<212> TYPE: DNA
<213> ORGANISM: human
<220> FEATURE:
<221> NAME/KEY: CDS
<222> LOCATION: (1)..(765)

<400> SEQUENCE: 9 atg aag aca ctc cag ttt ttc ttc ctt ttc tgt tgc tgg aaa gca atc      48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa      96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc      144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa      192
Tyr Cys Tyr Thr Arg Asp Leu Val Tyr Lys Asp Pro Ala Arg Pro Lys

```
                50                  55                  60
atc cag aaa aca tgt acc ttc aag gaa ctg gta tat gaa aca gtg aga      240
Ile Gln Lys Thr Cys Thr Phe Lys Glu Leu Val Tyr Glu Thr Val Arg
 65                  70                  75                  80 gtg ccc ggc tgt gct cac cat gca gat tcc ttg tat aca tac cca gtg      288
Val Pro Gly Cys Ala His His Ala Asp Ser Leu Tyr Thr Tyr Pro Val
                     85                  90                  95 gcc acc cag tgt cac tgt ggc aag tgt gac agc gac agc act gat tgt      336
Ala Thr Gln Cys His Cys Gly Lys Cys Asp Ser Asp Ser Thr Asp Cys
                100                 105                 110 act gtg cga ggc ctg ggg ccc agc tac tgc tcc ttt ggt gaa atg aaa      384
Thr Val Arg Gly Leu Gly Pro Ser Tyr Cys Ser Phe Gly Glu Met Lys
            115                 120                 125 gaa gga tcc gga tcg aac gcg acg ggg tca ggt tct aat gca act tca      432
Glu Gly Ser Gly Ser Asn Ala Thr Gly Ser Gly Ser Asn Ala Thr Ser
        130                 135                 140 aga tcc gga tcg aac gcg acg ggg tca ggt tct aat gca act tca gga      480
Arg Ser Gly Ser Asn Ala Thr Gly Ser Gly Ser Asn Ala Thr Ser Gly
145                 150                 155                 160 tcc act agt gct cct gat gtg cag gat tgc cca gaa tgc acg cta cag      528
Ser Thr Ser Ala Pro Asp Val Gln Asp Cys Pro Glu Cys Thr Leu Gln
                165                 170                 175 gaa aac cca ttc ttc tcc cag ccg ggt gcc cca ata ctt cag tgc atg      576
Glu Asn Pro Phe Phe Ser Gln Pro Gly Ala Pro Ile Leu Gln Cys Met
                180                 185                 190 ggc tgc tgc ttc tct aga gca tat ccc act cca cta agg tcc aag aag      624
Gly Cys Cys Phe Ser Arg Ala Tyr Pro Thr Pro Leu Arg Ser Lys Lys
            195                 200                 205 acg atg ttg gtc caa aag aac gtc acc tca gag tcc act tgc tgt gta      672
Thr Met Leu Val Gln Lys Asn Val Thr Ser Glu Ser Thr Cys Cys Val
        210                 215                 220 gct aaa tca tat aac agg gtc aca gta atg ggg ggt ttc aaa gtg gag      720
Ala Lys Ser Tyr Asn Arg Val Thr Val Met Gly Gly Phe Lys Val Glu
225                 230                 235                 240 aac cac acg gcg tgc cac tgc agt act tgt tat tat cac aaa tct taa      768
Asn His Thr Ala Cys His Cys Ser Thr Cys Tyr Tyr His Lys Ser
                245                 250                 255

<210> SEQ ID NO 10
<211> LENGTH: 255
<212> TYPE: PRT
<213> ORGANISM: human

<400> SEQUENCE: 10

Met Lys Thr Leu Gln Phe Phe Leu Phe Cys Cys Trp Lys Ala Ile
 1               5                  10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
        50                  55                  60

Ile Gln Lys Thr Cys Thr Phe Lys Glu Leu Val Tyr Glu Thr Val Arg
 65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110
```

```
Thr Val Arg Gly Leu Gly Pro Ser Tyr Cys Ser Phe Gly Glu Met Lys
        115                 120                 125

Glu Gly Ser Gly Ser Asn Ala Thr Gly Ser Gly Ser Asn Ala Thr Ser
130                 135                 140

Arg Ser Gly Ser Asn Ala Thr Gly Ser Gly Ser Asn Ala Thr Ser Gly
145                 150                 155                 160

Ser Thr Ser Ala Pro Asp Val Gln Asp Cys Pro Glu Cys Thr Leu Gln
                165                 170                 175

Glu Asn Pro Phe Phe Ser Gln Pro Gly Ala Pro Ile Leu Gln Cys Met
            180                 185                 190

Gly Cys Cys Phe Ser Arg Ala Tyr Pro Thr Pro Leu Arg Ser Lys Lys
        195                 200                 205

Thr Met Leu Val Gln Lys Asn Val Thr Ser Glu Ser Thr Cys Cys Val
210                 215                 220

Ala Lys Ser Tyr Asn Arg Val Thr Val Met Gly Gly Phe Lys Val Glu
225                 230                 235                 240

Asn His Thr Ala Cys His Cys Ser Thr Cys Tyr Tyr His Lys Ser
                245                 250                 255

<210> SEQ ID NO 11
<211> LENGTH: 145
<212> TYPE: PRT
<213> ORGANISM: human

<400> SEQUENCE: 11

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Ser Lys Ala Pro Pro Pro Ser Leu
        115                 120                 125

Pro Ser Pro Ser Arg Leu Pro Gly Pro Ser Asp Thr Pro Ile Leu Pro
    130                 135                 140

Gln
145

<210> SEQ ID NO 12
<211> LENGTH: 390
<212> TYPE: DNA
<213> ORGANISM: human
<220> FEATURE:
<221> NAME/KEY: CDS
<222> LOCATION: (1)..(387)

<400> SEQUENCE: 12 atg aag aca ctc cag ttt ttc ttc ctt ttc tgt tgc tgg aaa gca atc      48
Met Lys Thr Leu Gln Phe Phe Phe Leu Phe Cys Cys Trp Lys Ala Ile
1               5                   10                  15
```

```
tgc tgc aat agc tgt gag ctg acc aac atc acc att gca ata gag aaa        96
Cys Cys Asn Ser Cys Glu Leu Thr Asn Ile Thr Ile Ala Ile Glu Lys
         20                  25                  30 gaa gaa tgt cgt ttc tgc ata agc atc aac acc act tgg tgt gct ggc       144
Glu Glu Cys Arg Phe Cys Ile Ser Ile Asn Thr Thr Trp Cys Ala Gly
     35                  40                  45 tac tgc tac acc agg gat ctg gtg tat aag gac cca gcc agg ccc aaa       192
Tyr Cys Tyr Thr Arg Asp Leu Val Tyr Lys Asp Pro Ala Arg Pro Lys
 50                  55                  60 atc cag aaa aca tgt acc ttc aag gaa ctg gta tat gaa aca gtg aga       240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg       288
Val Pro Gly Cys Ala His His Ala Asp Ser Leu Tyr Thr Tyr Pro Val
             85                  90                  95 gcc acc cag tgt cac tgt ggc aag tgt gac agc gac agc act gat tgt       336
Ala Thr Gln Cys His Cys Gly Lys Cys Asp Ser Asp Ser Thr Asp Cys
         100                 105                 110 act gtg cga ggc ctg ggg ccc agc tac tgt tcc ttt ggt gaa atg aaa       384
Thr Val Arg Gly Leu Gly Pro Ser Tyr Cys Ser Phe Gly Glu Met Lys
     115                 120                 125 gaa taa                                                                390
Glu
```

<210> SEQ ID NO 13
<211> LENGTH: 129
<212> TYPE: PRT
<213> ORGANISM: human

<400> SEQUENCE: 13

```
Met Lys Thr Leu Gln Phe Phe Phe Leu Phe Cys Cys Trp Lys Ala Ile
 1               5                  10                  15

Cys Cys Asn Ser Cys Glu Leu Thr Asn Ile Thr Ile Ala Ile Glu Lys
             20                  25                  30

Glu Glu Cys Arg Phe Cys Ile Ser Ile Asn Thr Thr Trp Cys Ala Gly
         35                  40                  45

Tyr Cys Tyr Thr Arg Asp Leu Val Tyr Lys Asp Pro Ala Arg Pro Lys
 50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
             85                  90                  95

Ala Thr Gln Cys His Cys Gly Lys Cys Asp Ser Asp Ser Thr Asp Cys
         100                 105                 110

Thr Val Arg Gly Leu Gly Pro Ser Tyr Cys Ser Phe Gly Glu Met Lys
     115                 120                 125

Glu
```

<210> SEQ ID NO 14
<211> LENGTH: 351
<212> TYPE: DNA
<213> ORGANISM: human
<220> FEATURE:
<221> NAME/KEY: CDS
<222> LOCATION: (1)..(348)

<400> SEQUENCE: 14

```
atg gat tac tac aga aaa tat gca gct atc ttt ctg gtc aca ttg tcg        48
Met Asp Tyr Tyr Arg Lys Tyr Ala Ala Ile Phe Leu Val Thr Leu Ser
```

-continued

```
      1               5                  10                 15
gtg ttt ctg cat gtt ctc cat tcc gct cct gat gtg cag gat tgc cca    96
Val Phe Leu His Val Leu His Ser Ala Pro Asp Val Gln Asp Cys Pro
                 20                  25                  30 gaa tgc acg cta cag gaa aac cca ttc ttc tcc cag ccg ggt gcc cca   144
Glu Cys Thr Leu Gln Glu Asn Pro Phe Phe Ser Gln Pro Gly Ala Pro
         35                  40                  45 ata ctt cag tgc atg ggc tgc tgc ttc tct aga gca tat ccc act cca   192
Ile Leu Gln Cys Met Gly Cys Cys Phe Ser Arg Ala Tyr Pro Thr Pro
     50                  55                  60 cta agg tcc aag aag acg atg ttg gtc caa aag aac gtc acc tca gag   240
Leu Arg Ser Lys Lys Thr Met Leu Val Gln Lys Asn Val Thr Ser Glu
65                  70                  75                  80 tcc act tgc tgt gta gct aaa tca tat aac agg gtc aca gta atg ggg   288
Ser Thr Cys Cys Val Ala Lys Ser Tyr Asn Arg Val Thr Val Met Gly
                 85                  90                  95 ggt ttc aaa gtg gag aac cac acg gcg tgc cac tgc agt act tgt tat   336
Gly Phe Lys Val Glu Asn His Thr Ala Cys His Cys Ser Thr Cys Tyr
             100                 105                 110 tat cac aaa tct taa                                                351
Tyr His Lys Ser
         115
```

<210> SEQ ID NO 15
<211> LENGTH: 116
<212> TYPE: PRT
<213> ORGANISM: human

<400> SEQUENCE: 15

```
Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                 20                  25                  30

Glu Cys Thr Leu Gln Glu Asn Pro Phe Phe Ser Gln Pro Gly Ala Pro
         35                  40                  45

Ile Leu Gln Cys Met Gly Cys Cys Phe Ser Arg Ala Tyr Pro Thr Pro
     50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
             100                 105                 110

Tyr His Lys Ser
         115
```

<210> SEQ ID NO 16
<211> LENGTH: 16
<212> TYPE: PRT
<213> ORGANISM: human

<400> SEQUENCE: 16

```
Ser Gly Ser Asn Ala Thr Gly Ser Gly Ser Asn Ala Thr Ser Gly Ser
1               5                   10                  15
```

<210> SEQ ID NO 17
<211> LENGTH: 17
<212> TYPE: PRT
<213> ORGANISM: human

-continued

```
<400> SEQUENCE: 17

Gly Ser Gly Ser Asn Ala Thr Gly Ser Gly Ser Asn Ala Thr Ser Gly
1               5                   10                  15
Ser
```

What is claimed is:

1. A method for increasing a subject's fertility which comprises administering to the subject a synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser (SEQ. ID. NO:16) in an amount effective to enhance the subject's fertility.

2. A method for increasing a subject's fertility which comprises administering to the subject a synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ. ID. NO:16) in an amount effective to enhance the subject's fertility, wherein the β-FSH subunit, α-FSH subunit and polypeptide segment are covalently bound.

3. A method for increasing a subject's egg production which comprises administering to the subject a synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser (SEQ. ID. NO:16) in an amount effective to enhance the subject's egg production.

4. A method for increasing a subject's egg production which comprises administering to the subject a synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ. ID. NO:16) in an amount effective to enhance the subject's egg production, wherein the β-FSH subunit, α-FSH subunit and polypeptide segment are covalently bound.

5. A method for increasing the level of inhibin-A in a subject which comprises administering to the subject a synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser (SEQ. ID. NO:16) in an amount effective to increase the subject's inhibin-A level.

6. A method for increasing the level of inhibin-A in a subject which comprises administering to the subject a synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ. ID. NO:16) in an amount effective to increase the subject's inhibin A level, wherein the β-FSH subunit, α-FSH subunit and polypeptide segment are covalently bound.

7. A method for increasing the quality of an oocyte which comprises contacting the oocyte with a synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser (SEQ. ID. NO:16) in an amount effective to increase the quality of an oocyte.

8. A method for increasing the quality of an oocyte which comprises contacting the oocyte with a synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ. ID. NO:16) in an amount effective to increase the quality of an oocyte, wherein the β-FSH subunit, α-FSH subunit and polypeptide segment are covalently bound.

9. A method for increasing the quality of an oocyte in a subject which comprises administering to the subject a synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser (SEQ. ID. NO:16) in an amount effective to increase the quality of the oocyte in the subject.

10. A method for increasing the quality of an oocyte in a subject which comprises administering to the subject a synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ. ID. NO:16) in an amount effective to increase the quality of the oocyte in the subject, wherein the β-FSH subunit, α-FSH subunit and polypeptide segment are covalently bound.

11. The method of claims 1 or 2 wherein the subject is infertile and is to undergo in vitro fertilization.

12. The method of claim 11, wherein the subject is selected from the group consisting of a primate, a horse, a sheep, a bird, a bovine, a pig, a dog, a cat and a rodent.

13. The method of claim 12, wherein the subject is a human.

14. The method of claim 11, wherein the synthetic FSH is administered daily.

15. The method of claim 11, wherein the synthetic FSH is administered every other day.

16. The method of claim 11, wherein the synthetic FSH is administered every 6 to 8 days.

17. The method of claim 11, wherein the synthetic FSH is administered weekly.

18. The method of claim 11, wherein the synthetic FSH is administered intravenously, subcutaneously, intramuscularly, intraperitoneally, orally or topically.

* * * * *